US007189504B2

(12) United States Patent
Marnett et al.

(10) Patent No.: US 7,189,504 B2
(45) Date of Patent: Mar. 13, 2007

(54) COMPOSITIONS AND METHODS FOR DETECTING AND QUANTIFYING COX-2 ACTIVITY AND 2-ARACHIDONYLGLYCEROL METABOLITES

(75) Inventors: Lawrence J. Marnett, Nashville, TN (US); Kevin R. Kozak, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/923,637

(22) Filed: Aug. 7, 2001

(65) Prior Publication Data

US 2002/0064804 A1 May 30, 2002

Related U.S. Application Data

(60) Provisional application No. 60/302,975, filed on Jul. 3, 2001, and provisional application No. 60/223,665, filed on Aug. 7, 2000.

(51) Int. Cl.
*G01N 33/50* (2006.01)

(52) U.S. Cl. .......................................... 435/4; 436/501
(58) Field of Classification Search ................ 435/4, 435/25, 7.91, 7.1; 436/501, 64
See application file for complete search history.

(56) References Cited

U.S. PATENT DOCUMENTS

| | | | |
|---|---|---|---|
| 3,632,627 | A | 1/1972 | Gordon et al. |
| 4,675,281 | A | 6/1987 | Lands et al. |
| 5,047,354 | A | 9/1991 | Foegh et al. |
| 5,162,504 | A | 11/1992 | Horoszewicz |
| 5,459,239 | A | 10/1995 | O'Neill et al. |
| 5,474,903 | A | 12/1995 | Huland |
| 5,475,021 | A | 12/1995 | Marnett et al. |
| 5,543,297 | A | 8/1996 | Cromlish et al. |
| 5,589,575 | A | 12/1996 | Cohen et al. |
| 5,700,654 | A | 12/1997 | Roberts et al. |
| 5,731,343 | A | 3/1998 | Feng et al. |
| 5,756,092 | A | 5/1998 | Michelet et al. |
| 5,837,479 | A | 11/1998 | Young et al. |
| 5,858,694 | A | 1/1999 | Piazza et al. |
| 5,858,696 | A | 1/1999 | Roberts et al. |
| 5,874,235 | A | 2/1999 | Chan et al. |
| 5,891,622 | A | 4/1999 | Morrow et al. |
| 5,945,675 | A | 8/1999 | Malins |
| 5,958,978 | A | 9/1999 | Yamazaki et al. |
| 5,973,191 | A | 10/1999 | Marnett et al. |
| 5,995,645 | A | 11/1999 | Soenksen et al. |
| 5,999,843 | A | 12/1999 | Anbar |
| 6,045,773 | A | 4/2000 | Isakson et al. |
| 6,107,049 | A | 8/2000 | Allard et al. |
| 6,207,700 | B1 | 3/2001 | Kalgutkar et al. ......... 514/420 |

FOREIGN PATENT DOCUMENTS

| | | |
|---|---|---|
| CA | 71-125851 | 8/1973 |
| DE | 2155546 | 5/1972 |
| FR | 2159202 | 7/1973 |
| WO | WO 97/14679 | * 4/1997 |

OTHER PUBLICATIONS

Freshney, The Culture of Animal Cells, 1994, p. 5 and pp. 349–350.*
Yu et al (Journal of Biological Chemistry, 1997, vol. 272, pp. 21181–21186).*
Fritsche et al (2001, The Journal of Pharmacology and Experimental Therapeutics, vol. 299, pp. 468–467).*
Kalgutkar et al (Jan. 18, 2000, Proc. Natl. Sci. Acad. USA, vol. 97, pp. 925–930).*
Kozak et al (Oct. 27, 2000, J. Biol. Chem. vol. 275, pp. 33744–33749).*
Felder et al (1988, Annu. Rev. Pharmacol. Toxicol. vol. 38, pp. 179–200).*
Futaki et al (Dec. 1997, Inflammation Research 46: p. 496–502).*
LaPointe et al (Jan. 1998, Hypertension (Dallas) 31 (1 PART 2):p. 218–224).*
Hamiltin et al (Oct. 1997, British Journal of Pharmacology 122, Proc. Suppl:p. 22P).*
Belvisi et al (1997), British Journal of Pharmacology 120 (5):p. 910–916).*
Kalgutar, et al.; Biochemically based design of cyclooxygenase-2 (COX-2) inhibitors: Facile conversion of nonsteroidal antiinflammatory drugs to potent and highly selective COX-2 inhibitors; PNAS Jan. 18, 2000; 97(2) 925–930.
Kozak, et al.; Oxygenation of the Endocannabinoid, 2-Arachidonylglycerol, to Glyceryl Prostaglandins by Cyclooxygenase-2; The Journal of Biological Chemistry Oct. 27, 2000; 43:33744–33749.
Kozak, et al.; Amino Acid Determinants in Cyclooxygenase-2 Oxygenation of the Endocannabinoid 2-Arachidonylglycerol; JBP Papers in Press Jun. 11, 2001.

(Continued)

*Primary Examiner*—Karen A. Canella
(74) *Attorney, Agent, or Firm*—Stites & Harbison PLLC; Richard S. Myers, Jr.

(57) ABSTRACT

The present invention provides methods, compositions and kits for discriminating between COX-1 and COX-2 activity. In particular, the prevent invention provides for the detection and/or measurement of COX-2 activity in subjects, samples thereof, and in laboratory tests. The present invention discloses that 2-arachidonylglycerol is a COX-2 selective substrate which is metabolized by COX-2 to prostaglandin glycerol esters (PG-Gs) and that the diversity of PG-Gs parallels that of arachidonic acid derived metabolites of COX. The present invention also provides certain novel COX-2 selective metabolites including prostaglandin $I_2$-glycerol ester ($PGI_2$-G) and 6-keto-prostaglandin $F_{1\alpha}$-glycerol ester. Methods and kits are described for detecting COX-2 activity comprising detecting PG-Gs (including the novel PG-Gs disclosed herein). Uses for these methods and kits include the detection and monitoring of inflammation and tumors or cancer. Additional uses include the monitoring of test agents in assays to screen for COX-2 specific inhibitors and other laboratory uses.

37 Claims, 11 Drawing Sheets

OTHER PUBLICATIONS

Lands, et al.; Phospholipid precursors of prostaglandins; Biochem. Biophys. Acta 1968; 164:426–429.

Prescott; A thermatic series on oxidation of lipids as a source of messengers; J.Biol. Chem.; 274:22901.

Smith, et al.; Prostaglandin Endoperoxide H Synthases (Cyclooxygenases)–1 and –2; The Journal of Biological Chemistry Dec. 27, 1996; 271:52:33157–33160.

So, et al.; The dynamics of prostaglandin H synthases. Studies with prostaglandin h synthase 2 Y355F unmask mechanisms of time–dependent inhibition and allosteric activation; J. Biol. Chem; 273:5801–5807.

Tanha, et al.; Optimal Design Features of Camelized Human Single–Domain Antibody Libraries; JBP Papers in Press May 2, 2001.

Tokumoto, et al.; Specificity of Prostagland D2 Binding to Synaptic Membrane Fraction of Rat Brain; Brain Research 1986; 362:114–121.

Tsujii, et al.; Cyclooxygenase–2 expression in human colon cancer cells increases metastatic potential; Proc. Natl Acad. Sci. Apr. 1997; 94:3336–3340.

Vonkeman, et al.; The action of prostaglandin synthetase on 2–arachidonyl–lecithin; Biochem. Biophys. Acta; 164:430–432.

Woodward, et al.; The pharmacology of bimatoprost (Lumigan); Surv. Ophthalmol.; 45 Suppl 4; S337–345.

Yu, et al; Synthesis of Prostaglandin E2 Ethanolamide from Anandamide by Cyclooxygenase–2; The Journal of Biological Chemistry Aug. 22, 1997; 272(34):21181–21186.

* cited by examiner

ARACHIDONIC ACID $R_1 = CH_2CH=CH(CH_2)_3CO_2H$; $R_2 = C_5H_{11}$; $AH_2$ = reducing substrate

2-ARACHIDONYLGLYCEROL (2-AG)

COMPOSITIONS AND METHODS FOR DETECTING AND QUANTIFYING COX-2 ACTIVITY AND 2-ARACHIDONYLGLYCEROL METABOLITES

APPLICATION FOR UNITED STATES LETTERS PATENT

This application claims benefit of U.S. Patent Application Ser. No. 60/223,665 filed Aug. 7, 2000, entitled "Method for in vitro and in vivo determination of COX-2 activity" and U.S. Patent Application Ser. No. 60/302,975 filed Jul. 03, 2001, entitled "COX-2 Assays"; each application incorporated herein by reference.

Be it known that we, Lawrence J. Marnett, a citizen of the United States, residing at 1884 Laurel Ridge Drive, Nashville, Tenn. 37215, and Kevin R. Kozak, a citizen of the United States, residing at 1906 Chet Atkins Blvd. #705, Nashville, Tenn. 37212; have invented new and useful "Compositions and Methods for Detecting and Quantifying COX-2 Activity and 2-Arachidonylglycerol Metabolites."

GOVERNMENT SUPPORT CLAUSE

This invention is made with federal grant money from the National Foundation for Cancer Research. The United States Government has certain rights in this invention.

TABLE OF CONTENTS

1. Background of the Invention
1.1 Field of the Invention
1.2 Description of the Relevant Art
2. Summary of the Invention
3. Brief Description of the Drawings
4. Detailed Description of the Invention
4.1 Definitions
4.2.1 Cyclooxygenases and Prostaglandins
4.2.2 COX-2 Selective Metabolism of 2-AG to PG-Gs
4.3 Detecting COX-2 Activity
4.4 Measuring Glyceryl Prostaglandins
4.4.1 Use of a Standard
4.4.2 Detection and Measuring Devices
4.4.3 Separation Devices
4.4.4 Subjects
4.4.5 Samples
4.4.6 Antibodies
4.5 COX-2 and Inflammatory Diseases
4.6 COX-2 and Cancer
4.7 COX-2 and Research
4.8 Kits
4.9 Certain Novel PG-Gs
5.0 Examples
5.1 Example 1
5.2 Example 2
5.3 Example 3
5.4 Example 4
5.5 Example 5
5.6 Example 6
5.7 Example 7
5.8 Example 8
5.9 Example 9
5.10 Example 10
5.11 Example 11
5.12 Example 12

1. BACKGROUND OF THE INVENTION

1.1 Field of the Invention

The present invention relates generally to the cyclooxygenases and their roles in cancer and inflammation. More particularly, this invention pertains to methods and articles of manufacture for detecting and measuring COX-2 activity by detecting and measuring COX-2 specific enzymatic products including glyceryl-prostaglandins.

1.2 Description of the Related Art

COX, or prostaglandin endoperoxide synthase enzyme (cyclooxygenase, COX, EC 1.14.99.1), catalyzes the conversion of arachidonic acid to prostaglandin (PG) $H_2$. Two isoforms of COX are known, COX-1 and COX-2. COX-1 is constitutively expressed. COX-2, however, is inducible in a variety of cells, especially those of the central nervous and immune systems (Masferrer et al. 1994, Proc. Natl. Acad. Sci. USA 91:3228–3232; Vane et al. 1994, Proc. Natl. Acad. Sci. USA 91:2046–2050; Kennedy et al. 1993, Biochem. Biophys. Res. Commun. 197:494–500). Certain changes in COX-2 activity are associated with a variety of human inflammatory diseases. These diseases include, but are not limited to, acute appendicitis, asthma, myocardial infarction, certain immunological disease processes, infection, malignancy, endotoxemia and reperfusion injury. In addition, inappropriate COX-2 expression or overexpression is associated with certain types of cancers, including, but not limited to, carcinoma of the colon, rectum, stomach, esophagus, lung, and skin. The amount of COX-2 expression is related to the cancer stage and grade (Fosslien, E, et al. 2000, Ann. Clin. Lab. Sci. 30:3–21). COX-2 has become a major pharmaceutical target for developing treatments for these and other diseases. Methods of detecting and measuring COX-2 activity are highly desired.

Yu et al. (1997) J. Biol. Chem. 272:21181–21186, describes the enzymatic conversion of arachidonyl ethanolamide (anandamide, AEA), to $PGE_2$-ethanolamide in cell lines expressing COX-2 but not COX-1.

U.S. Pat. No. 5,543,297 to Cromlish et al., describes measuring total COX activity (COX-1 activity and COX-2 activity) in separate samples, with and without a COX-2 specific inhibitor, and then indirectly estimating COX-2 specific activity by subtracting the total COX activity observed with the inhibitor from the total COX activity observed without the inhibitor. One major weakness of this method is that the dynamics of enzymatic inhibition change based upon numerous variables including time, temperature, concentration, specificity, sample preparation, etc.

U.S. Pat. No. 5,475,021 to Marnett et al. describes a method of measuring the activity of purified COX-2 by measuring $O_2$-uptake during catalysis. This method requires purification of the enzyme.

U.S. Pat. No. 6,045,773 to Isakson et al., describes a method for measuring COX-2 expression in a mammal by administering a positron-emitting radioisotope-labeled COX-2 selective binding agent to the mammal and then detecting the label by positron-emission tomography (PET). Weaknesses of this method include the invasive nature and expense of PET equipment. In addition, the method only localizes COX-2 protein but does not detect or measure activity.

What is needed, then, is a less-invasive, method of selectively detecting and measuring COX-2 activity in biological samples without the need to purify the enzyme.

2. SUMMARY OF THE INVENTION

The present invention provides, in part, novel compositions, assays and kits for detecting and/or measuring COX-2 activity. The present inventors discovered that 2-aracodonylglycerol (2-AG) is a substrate of the COX-2 enzyme, but not a significant substrate of the COX-1 enzyme.

Certain aspects of the present invention provide a system for detecting and/or quantifying COX-2 activity comprising detecting and/or measuring COX-2 selective metabolites present in the system (e.g., a patient or sample thereof). In certain embodiments, the COX-2 selective metabolite comprises and prostaglandin glycerol ester (PG-G) and in preferred embodiments a 6-keto-prostaglandin $F_{1a}$-glycerol ester (6-keto-PGF$_{1a}$-G). Additional aspects of the present invention provide certain novel PG-Gs and a variety of labeled PG-Gs useful for the detection of COX-2 activity. A preferred system for detecting and measuring a PG-G comprises liquid chromatography/mass spectrometry (LC/MS).

Certain aspects of the present invention, provide methods and compositions for detecting tumors, cancer, and inflammation and methods and compositions for monitoring the same. Certain embodiments provide a method of detecting a disease (including inflammation, cancer, neurodegeneration, and/or hyperalgesia), comprising detecting a COX-2 selective metabolite in a subject or sample thereof, wherein the presence of the metabolite indicates the presence of the disease. Certain embodiments provide a method of measuring, staging, or grading a disease (including a disorder) (especially inflammation and/or cancer), comprising measuring an amount of a COX-2 selective metabolite in a subject or sample thereof, wherein the amount of the metabolite is correlated to the amount, level, stage, and/or grade of the disease, such as inflammation or cancer.

Still another aspect of the present invention provides a system for detecting and/or quantifying metabolites of COX-2 catalysis of 2-AG including direct reaction products and additional metabolites generated both enzymatically and non-enzymatically downstream of the COX-2 catalysis reaction with 2-AG.

A further aspect of the present invention provides a system for relating the presence and/or amount of COX-2 generated 2-AG metabolites to the activity of the COX-2 enzyme in the subject or system under study.

Certain embodiments of the present invention provide assays and kits useful for laboratory and clinical determinations of COX-2 specific activity, 2-AG metabolites of COX-2 action, and labeled COX-2 metabolites of 2-AG useful, in part, to standardize such assays and kits. In general, COX-2 activity detection and measurement is accomplished by detecting and/or measuring the COX-2 specific enzymatic glyceryl-prostaglandin products. The ability to detect and accurately measure COX-2 specific activity is important for patients with a variety of inflammatory and cancerous diseases. The present invention provides novel compositions and methods for diagnosing and monitoring these disease processes, for evaluating the effectiveness of therapy, and for developing new treatments of these diseases, among other uses.

In certain embodiments of the present invention, the amount of PG-G measured in the sample is compared to a standard, including labeled PG-Gs (e.g., deuterated PGE$_2$-G and comparison by LC/MS), wherein the amount of PG-G is associated with the amount or level of COX-2 activity. In certain embodiments of the present invention, the amount of COX-2 activity is associated with inflammation or cancer in the subject.

3. BRIEF DESCRIPTION OF THE DRAWINGS

Figure 21:
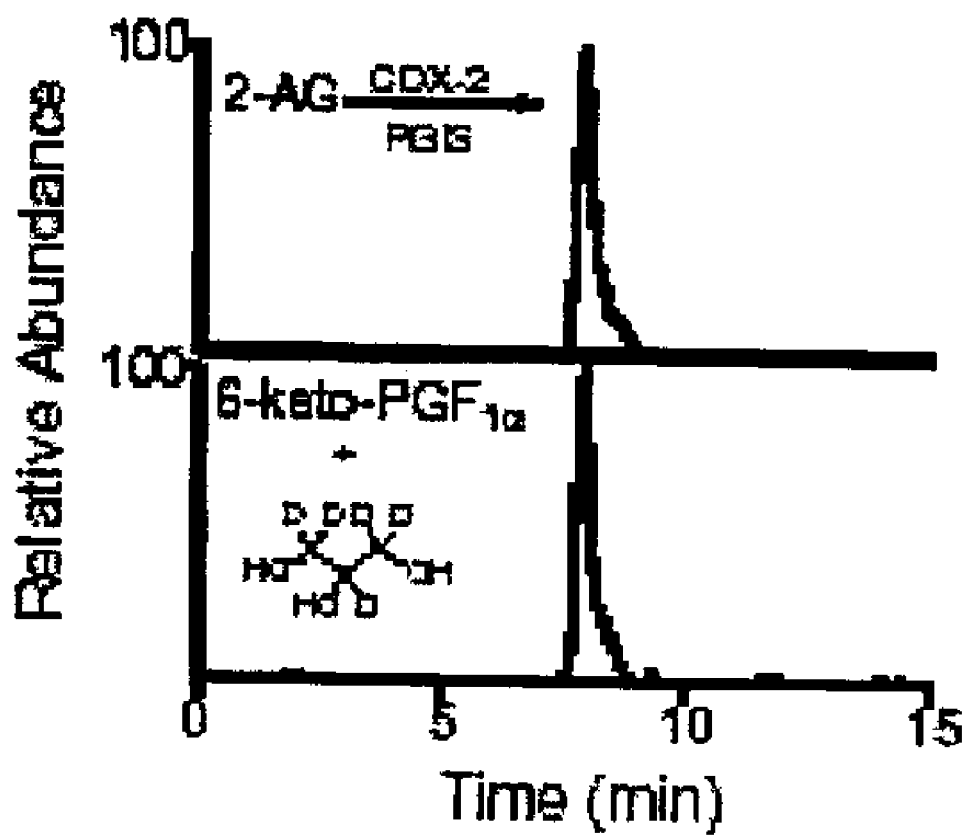

FIG. 21 is a liquid chromatography mass spectrometry (LC/MS) selected-ion chromatogram confirming the manufacture of 6-keto-PGF$_{1a}$-G from the sequential action of COX-2 and PGIS on 2-AG (and spontaneous non-enzymatic reaction from the PGI$_2$-G thus formed, top panel) and the manufacture of isotopically labeled 6-keto-PGF$_{1a}$-G by reacting 6-keto-PGF$_{1a}$ with deuterated glycerol (bottom panel).

4. DETAILED DESCRIPTION OF THE INVENTION

The present invention provides novel compositions, methods and articles of manufacture for detecting and measuring cyclooxygenase-2 (COX-2) activity in a subject or a sample thereof. Certain embodiments of the present invention provide compositions and methods of detecting and measuring PG-Gs, for which the committed steps of synthesis was discovered by the present inventors to be catalyzed by the COX-2 enzyme. In certain embodiments, the relative or absolute amount of PG-G is correlated to an amount of COX-2 enzyme activity. Certain embodiments of the present invention provide novel kits for detecting and measuring COX-2 activity, methods of identifying tumors in a subject and measuring relative tumor severity (i.e., stage or grade), and methods of detecting inflammation in a subject and measuring relative inflammation severity. No aspect, embodiment or element, of the present invention is limited by theory or mechanism.

4.1 Definitions

In case of conflict, the present document, including definitions, will control.

Unless otherwise indicated, materials, methods and examples described herein are illustrative only and not intended to be limiting. All references, citations, articles, publications, patents, and the like provided in this patent application are incorporated herein by reference, in their entirety.

The term in vivo includes the meaning of processes occurring in an animal, in tissue or cell culture, or in samples taken from an animal or culture.

The term in vitro includes the meaning of processes occurring in systems wholly or partially purified from the natural environment, such as with purified enzymes or defined enzyme systems.

Purified means partially or wholly isolated away from the natural milieu of factors normally associated with a particular macromolecular species. In certain embodiments, the purified factor comprises 50 percent or more (on a molar basis) of all macromolecular species present in the isolated form. In certain embodiments, a purified composition will comprise more than about 80 percent of all macromolecular species present. In certain preferred embodiments, a purified composition comprises more than about 90 percent of all macromolecular species present. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species. In non-liquid compositions, "purified" is based upon dry weight and the same percent purities stated above are embodied.

A COX-2 selective substrate is a substrate that is transformed to an enzymatic reaction product by the COX-2 enzyme; but is not transformed, or is not significantly transformed, to a reaction product by the COX-1 enzyme. It is most preferred that a COX-2 selective substrate of the present invention is not enzymatically transformed to a reaction product by COX-1. In certain embodiments, COX-1 may have some activity on the COX-2 selective substrate, but it is not significant relative to the COX-2 activity. Relatively insignificant activity can be determined, for example, by measuring the ratio of substrate oxygenation using purified COX-1 and COX-2.

In certain embodiments, the ratio of COX-1 activity versus COX-2 activity for a COX-2 selective substrate, expressed as a percentage, is about 50% or less; in certain embodiments, 40% or less; in certain embodiments, 30% or less; in certain embodiments, 25% or less; in certain embodiments, 20% or less; in certain embodiments, 10% or less; in certain embodiments, 5% or less; in certain embodiments, 3% or less; in certain embodiments, 2% or less; and in certain preferred embodiments 1% or less. The lower the percentage (above), the more preferred the embodiment. A highly preferred COX-2 selective substrate is metabolized by COX-2, but is not metabolized by COX-1.

The terms "COX-2 specific substrate" and "COX-2 selective substrate" are used interchangeably herein.

In general, enzyme activity refers to the rate at which substrate is consumed or product is formed in an enzymatic reaction under a given set of reaction conditions. The Standard International (SI) unit for enzyme activity is an enzyme unit (U) and is defined as the amount of enzyme needed to produce 1 µmole product/minute. A unit may be defined differently herein (e.g., the amount of enzyme needed to produce 1 nmoles product per minute or the amount of enzyme needed to consume 1 µmole substrate per minute). Additional determinations of enzyme activity can be compared when utilizing similar or preferably identical reaction conditions. It is understood that reaction conditions can be changed and a new enzyme activity scale determined (e.g., by generating a standard curve of enzyme activity and use thereof, a process which is known to one of ordinary skill in the art). The specific activity of a particular enzyme preparation refers to the total enzyme units divided by the total amount of protein present in the preparation. A preferred unit of specific activity is U per mg of protein (U/mg).

The compound 2-arachidonylglycerol is a COX-2 selective substrate. COX-2 is shown herein to transform 2-arachidonylglycerol to prostaglandin $H_2$-glycerol ester ($PGH_2$-G). Downstream metabolites of COX-2 action on 2-AG are referred to herein as prostaglandin glycerol esters (PG-Gs). As defined herein, PG-Gs include, but are not limited to: prostaglandin $H_2$-glycerol ester ($PGH_2$-G), prostaglandin $E_2$-glycerol ester ($PGE_2$-G), 15-keto-$PGE_2$-G, 13,14-dihydro-15-keto-$PGE_2$-glycerol ester, prostaglandin $D_2$-glycerol ester ($PGD_2$-G), prostaglandin $F_{2\alpha}$-glycerol ester ($PGF_{2\alpha}$-G), thromboxane $A_2$-glycerol ester ($TxA_2$-G), thromboxane $B_2$-glycerol ester ($TxB_2$-G), prostaglandin $I_2$-glycerol ester ($PGI_2$-G, also referred to herein as prostacyclin glycerol ester), 6-keto-$PGF_{1\alpha}$-G, 11-hydroxy-eicosatetranoic glycerol ester (11-HETE-G), 15-HETE-G, prostaglandin $A_2$-glycerol ester ($PGA_2$-G), prostaglandin $B_2$-glycerol ester ($PGB_2$-G), and 12-hydroxyheptadeca-5,8,10-trienoic-glycerol ester (HHT-G).

As used herein, PG-Gs are also included in the meaning of COX-2 selective metabolites and COX-2 specific metabolites.

The terms "prostaglandin glycerol ester" and "glyceryl-prostaglandin" are used interchangeably herein.

As used herein, references to COX include both COX-1 and COX-2.

Tumor type typically references the tissue of tumor origin, but can also refer to the current tissue in which a tumor is located (e.g., colon cancer, liver cancer, or pancreatic cancer). The stage and grade of a tumor is related to severity and medical definitions of stages and grades within a continuum are known in the art for each tumor or cancer type. Each specialty within oncology (e.g., hematology, colorectal, liver, pancreatic, lung, brain, dermatology, etc.) may have a particular standard for the stage and grade scale of the tumors used within that clinical specialty, known to one of skill in that art, which varies from the general definitions of tumor stage and grade provided below.

Tumor grade is determined by the appearance of the tumor under the microscope and how quickly the tumor is likely to grow and spread. In general, grading systems are different for each type of cancer, but are known to one of ordinary skill in the art. For example, grade I tumors are the least malignant appearing, grade II tumors are moderately differentiated with a moderately malignant appearance, grade III tumors are less differentiated and show enhanced signs of tissue invasion, and grade IV tumors display the least differentiation and are the most malignant appearing. The grade of a tumor is determined by one of ordinary skill in the art.

The state of a tumor refers to the extent of a cancer, how advanced the tumor is in the patient (e.g., whether the disease has spread from the original site to other parts of the body). The stage of a tumor is generally determined by radiographic studies such as a computed tomography (CT) scan. magnetic resonance (MRI) imaging and/or ultrasound. Tumor staging is determined by one of ordinary skill in the art and can vary by tumor type or as a field advances, standard staging practices may change. Certain definitions of stages for various cancers are provided in the Dictionary of Cancer Terms which is a service of the National Cancer Institute. A physical location for inquiry or obtaining a copy of the Dictionary of Cancer Terms is: NCI Public Inquiries; Building 31; Room 10A03; 31 Center Drive, MSC 2580; Bethesda, MD 20892-2580.

Staging refers to performing exams and tests to learn the extent of the cancer within the body, especially whether the disease has spread from the original site to other parts of the body.

Certain abbreviations include: cyclooxygenase (COX), cyclooxygenase-1 (COX-1), cyclooxygenase-2 (COX-2), prostaglandin (PG), prostaglandins (PGs), arachidonylglycerol (AG), 2-arachidonylglycerol (2-AG), prostaglandin glycerol ester (PG-G).

4.2.1 Cyclooxygenases and Prostaglandins

Figure 1:
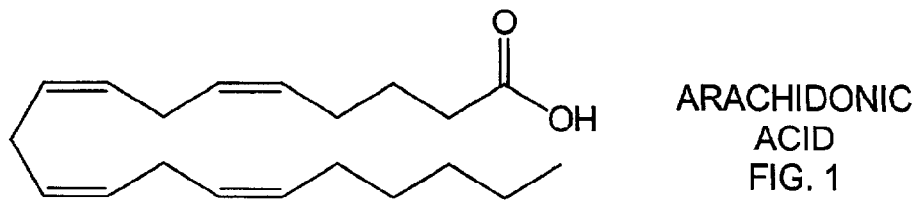
FIG. 1 is a diagram of the structure of arachidonic acid (AA).
Figure 2:
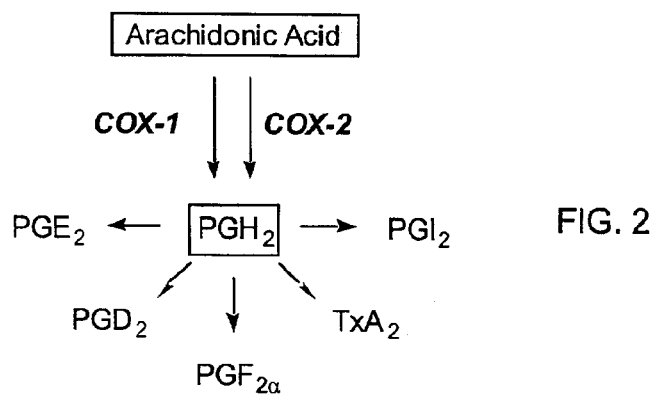
FIG. 2 is a general diagram of the COX biosynthetic pathway of prostaglandins and thromboxane from arachidonic acid.
Figure 3:
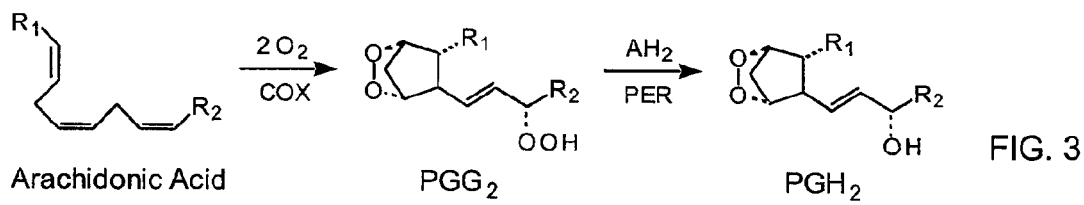
FIG. 3 is a diagram of the COX biosynthetic pathway of arachidonic acid to PGH$_2$, showing the chemical structure of the substrate and the metabolites.
Figure 4:
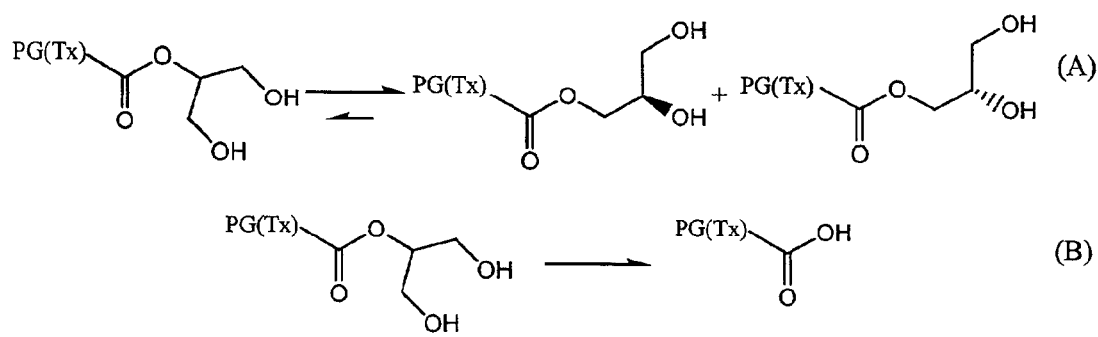
FIG. 4 is a diagram of certain general metabolic pathways for 2-glycerol esters.

Cyclooxygenase (COX; prostaglandin endoperoxide synthase, EC 1.14.99.1) catalyzes the bis-dioxygenation of arachidonic acid (FIG. 1) generating prostaglandin (PG) $H_2$ (FIGS. 2–3). This is the committed step in prostaglandin and thromboxane biosynthesis. Two isoforms of COX have been cloned from animal cells including constitutively expressed COX-1 (DeWitt, D. L., and Smith, W. L. 1988, *Proc. Natl. Acad. Sci. USA*, 85:1412–1416; Merlie, et al. 1988, *J. Biol. Chem.*, 263:3550–3553; Yokoyama, et al. 1988, *FEBS Lett.*, 231:347–351; DeWitt, et al. 1990, *J. Biol. Chem.*, 265:5192–5198; and Yokoyama, C. and Tanabe, T. 1989, *Biochem. Biophys. Res. Commun.*, 165:888–894) and inducibly expressed COX-2 (Xie, et al. 1991, *Proc. Natl. Acad. Sci. USA*, 88:2692–2696; Kujubu, et al. 1991, *J. Biol. Chem.*, 266:12866–12872; O'Banion, et al. 1991, *J. Biol. Chem.*, 266:23261–23267; Hla, T. and Nielson, K. 1992, *Proc. Natl. Acad. Sci. USA*, 89:7384–7388; Jones, et al. 1993, *J. Biol. Chem.*, 268:9049–9054; and Feng, et al. 1993, *Arch. Biochem. Biophys.*, 307:361–368).

Prostaglandins produced as a result of the activity of COX are known to have numerous physiological functions. These functions include the antithrombogenic action of prostacyclin released by the vascular endothelium and the cytoprotective effect of prostaglandins produced by the gastric mucosa (Whittle, et al. 1980, *Nature*, 284:271–273). COX-2 is typically expressed following the activation of normal cells and certain atypically proliferating cells, especially by various pro-inflammatory agents including certain cytokines (Hla, T. and Nielson, K. 1992, *Proc. Natl. Acad. Sci. USA*, 89:7384–7388; Feng, et al. 1993, *Arch. Biochem. Biophys.*, 307:361–368), endotoxin (Lee, et al. 1992, *J. Biol. Chem.*, 267:25934–25938) and certain mitogens (Kujubu, et al. 1991, *J. Biol. Chem.*, 266:12866–12872; O'Banion, et al. 1991, *J. Biol. Chem.*, 266:23261–23267; and Hla, T. and Nielson, K. 1992, *Proc. Natl. Acad. Sci. USA*, 89:7384–7388).

Prostaglandins (PGs) represent a class of substances produced in a wide variety of cells. In general, PGs act on the cells that produce them, on neighboring cells, or over short distances and can be classified as autocrine or paracrine hormones. PGs and their relatives are usually thought of as potent local hormones (autocrine and paracrine) and act over short distances because they have relatively short half-lives in aqueous environments. PGs, and related compounds, prostacyclin ($PGI_2$), thromboxanes (TX), leukotrienes (LT), and lipoxins (LP), derive from fatty acids stored in cellular membranes as phospholipids or triglycerides, especially arachidonic acid (FIGS. 1–3). A series of enzymatic and/or non-enzymatic reactions culminate in the release of prostaglandin products in the cell.

Prostaglandins and related metabolites are generally derived from fatty acids, usually arachidonic acid, with an open chain, 20-carbon structure (FIG. 1). Prostaglandins resemble hairpins with a five-membered ring and two chains extending from the ring. In general, substituents on the five-membered ring determine the subclass and activity of the prostaglandins.

4.2.2 COX-2 Selective Metabolism of 2-AG to PG-Gs

The present inventors have discovered that prostaglandin glycerol esters (PG-Gs) are synthesized enzymatically, including in vivo in mammals, by a COX-2 specific mechanism (see, for example, FIGS. 4–7). Certain aspects of the present invention include that detection and/or measurement of PG-G in a system, subject, or sample of a subject is/are useful for detecting and/or measuring COX-2 specific activity in the system, subject, and/or sample.

The inventors discovered that 2-arachidonylglycerol (2-AG, FIG. 8) is a COX-2 selective substrate. One aspect of the present invention is that COX-2 catalyzes the conversion of 2-AG to glyceryl-prostaglandin $H_2$ ($PGH_2$-G). In certain embodiments, the $PGH_2$-G is subsequently enzymatically and/or non-enzymatically transformed to one or more additional PG-Gs. Specifically, the inventors have discovered that COX-2 combined with certain enzymes downstream of COX in the known COX-arachidonic acid metabolic pathways are capable of transforming 2-AG into a spectrum of PG-Gs each of which, in general, has a PG analog in the COX-arachidonic acid metabolic pathways. The inventors also discovered that non-enzymatic reactions also occur among the PG-Gs which are analogous to the nonenzymatic reactions known to occur in the COX-arachidonic acid metabolic pathways. Thus, in general, PG-Gs that are analogous to each of the known PGs are generated by the combined action of COX-2 and downstream enzymatic and nonenzymatic reactions (e.g., see FIGS. 5–7). In addition, prostaglandin and thromboxane glycerol esters are susceptible to nonenzymatic isomerization of the glycerol moiety (FIG. 4a) as well as enzymatic hydrolysis (FIG. 4b).

Figure 5:
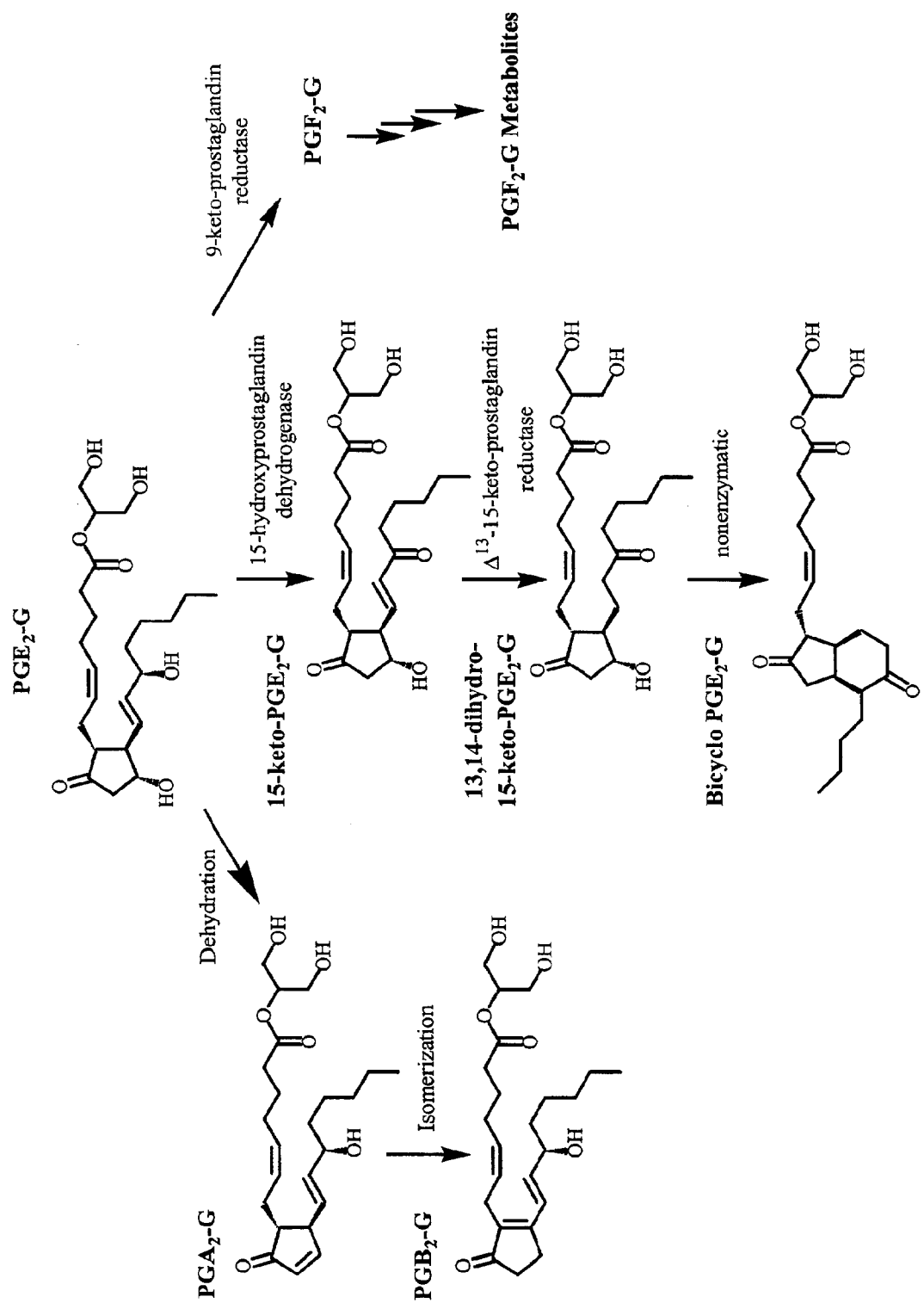
FIG. 5 is a diagram of the metabolism of PGE$_2$-G illustrating certain type-specific enzymatic and nonenzymatic biotransformations of prostaglandin glycerol esters.

It is disclosed herein, that prostaglandin and thromboxane glycerol esters undergo type-specific enzymatic and nonenzymatic biotransformations, which are discovered by the present inventors to parallel the known metabolic pathways for the free-acid prostaglandins and thromboxanes, in general. FIG. 5 provides an example of additional COX-2 selective prostaglandin-glycerol ester metabolites. In this example, $PGE_2$-G is metabolized by 15-hydroxyprostaglandin dehydrogenase to yield 15-keto-$PGE_2$-G, which, in certain embodiments, is transformed by $\Delta^{13}$-15-keto-prostaglandin reductase, to generate 13,14-dihydro-15-keto-$PGE_2$-G. In certain embodiments, the later product undergoes nonenzymatic reaction to yield bicycle-PGE$_2$-G. In certain embodiments, the PGE$_2$-G undergoes dehydration to yield PGA$_2$-G. In certain embodiments, the PGA$_2$-G undergoes isomerization to yield PGB$_2$-G. In certain embodiments, PGE$_2$-G undergoes transformation by 9-keto-prostaglandin reductase to yield PGF$_2$-G which is converted, in certain embodiments, to additional PGF$_2$-G metabolites. In certain embodiments, a given reaction product of PGE$_2$-G metabolism (whether generated in vitro or in vivo) comprises a glycerol ester analogue of a corresponding PGE$_2$ metabolite.

In general, the inventors contemplate that a reaction scheme comparable to the example scheme shown in FIG. 5 can be readily determined by one of ordinary skill in the art, in light of the present disclosure for each additional PG-G described herein by comparison to analogous metabolic products of the free-acid prostaglandins, thromboxanes, and side products. For example, similar schemes to that shown in FIG. 5 are contemplated, in certain embodiments, for metabolites of PGF$_{2a}$-G, PGD$_2$-G, PGI$_2$-G, the thromboxane glycerol esters, the HETE glycerol esters, and the HHT glycerol esters wherein the reactions for the particular scheme parallel that of metabolites derived from the free fatty acids (including substitution of the downstream enzymes involved with PGE$_2$ metabolism for the appropriate downstream enzymes of the analogous pathway under consideration (e.g., PGI$_2$-G is analogous to PGI$_2$), as would be apparent to one of ordinary skill in the art, in light of the present disclosure). Also, oxidative transformations including P$_{450}$-mediated ω-oxidation (e.g., C-19, C-20) are contemplated in certain embodiments.

The chemical synthesis of certain glycerol prostenoic acid compositions from glycerol and prostenoic acid is described in U.S. Pat. No. 3,632,627 to Gordon et al. and U.S. Pat. No. 3,746,728 to Gordon et al., each patent incorporated herein by reference.

4.3 Detecting COX-2 Activity

The present inventors have discovered that the activity of COX-2 in a system can be determined (i.e., detected, measured, assayed, etc.) by analyzing COX-2 selective metabolism in the system. For example, in certain embodiments, the presence of a COX-2 selective metabolite in a system demonstrates an activity of the COX-2 enzyme in the system. The present system provides methods and compositions for discriminating between COX-1 enzyme activity and COX-2 enzyme activity and; thus, provides for the detection and/or measurement of COX-2 selective enzyme activity.

As used in certain embodiments herein, the activity of a COX-2 enzyme includes, but is not limited to: a COX-2 catalyzed consumption of a substrate (preferably a COX-2 selective substrate) and a formation of a product (preferably a COX-2 selective metabolite). For example, the COX-2 mediated transformation of 2-AG to PGH$_2$-G is an activity of the COX-2 enzyme. In another example, the COX-2 selective metabolite is an arachidonylethanolamide (AEA). In still another example, the detection of PGH$_2$-G or anther PG-G in a sample of the subject is indicative of an activity of a COX-2 enzyme. COX-1 does not form significant amounts of PG-G products.

One aspect of the present invention provides a method of detecting an activity of a COX-2 enzyme in a subject, comprising obtaining a sample of the subject and detecting a metabolite of a COX-2 selective substrate in the sample. The presence of the metabolite in the sample indicates that the COX-2 enzyme is active in the subject. In certain embodiments, an amount of the metabolite in the sample is measured and can be related to the activity of the COX-2 enzyme in the subject. In certain embodiments, the measurement is semi-quantitative (more levels or values of detection than 2 (yes or no), for example: –, +, ++, +++, and ++++ levels of activity).

Figure 6:
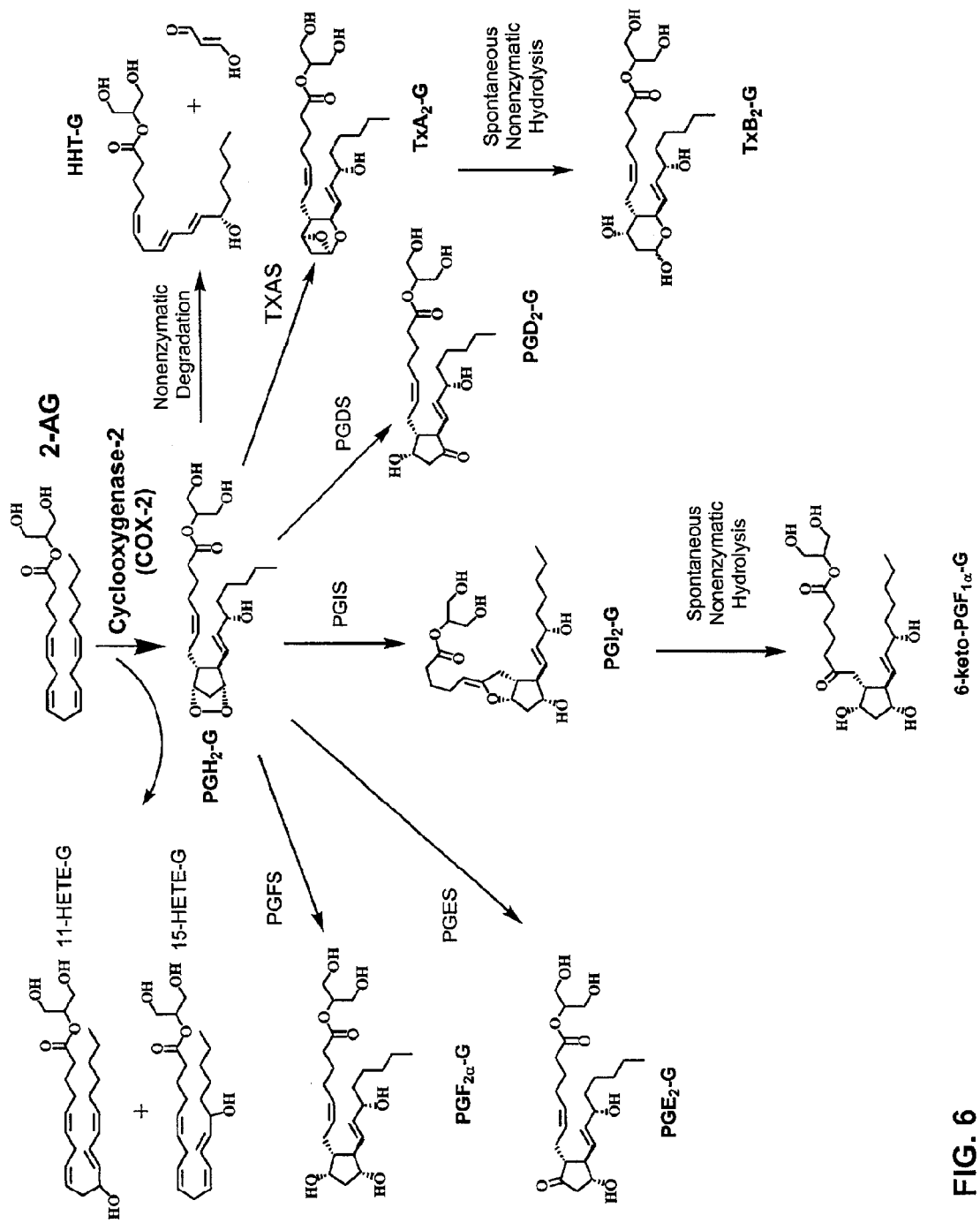
FIG. 6 is a diagram of certain prostaglandin glycerol esters generated enzymatically (e.g., in vivo) following COX-2 action on 2-AG and certain non-enzymatic derivatives of these products (e.g., spontaneous hydrolysis).
Figure 7:
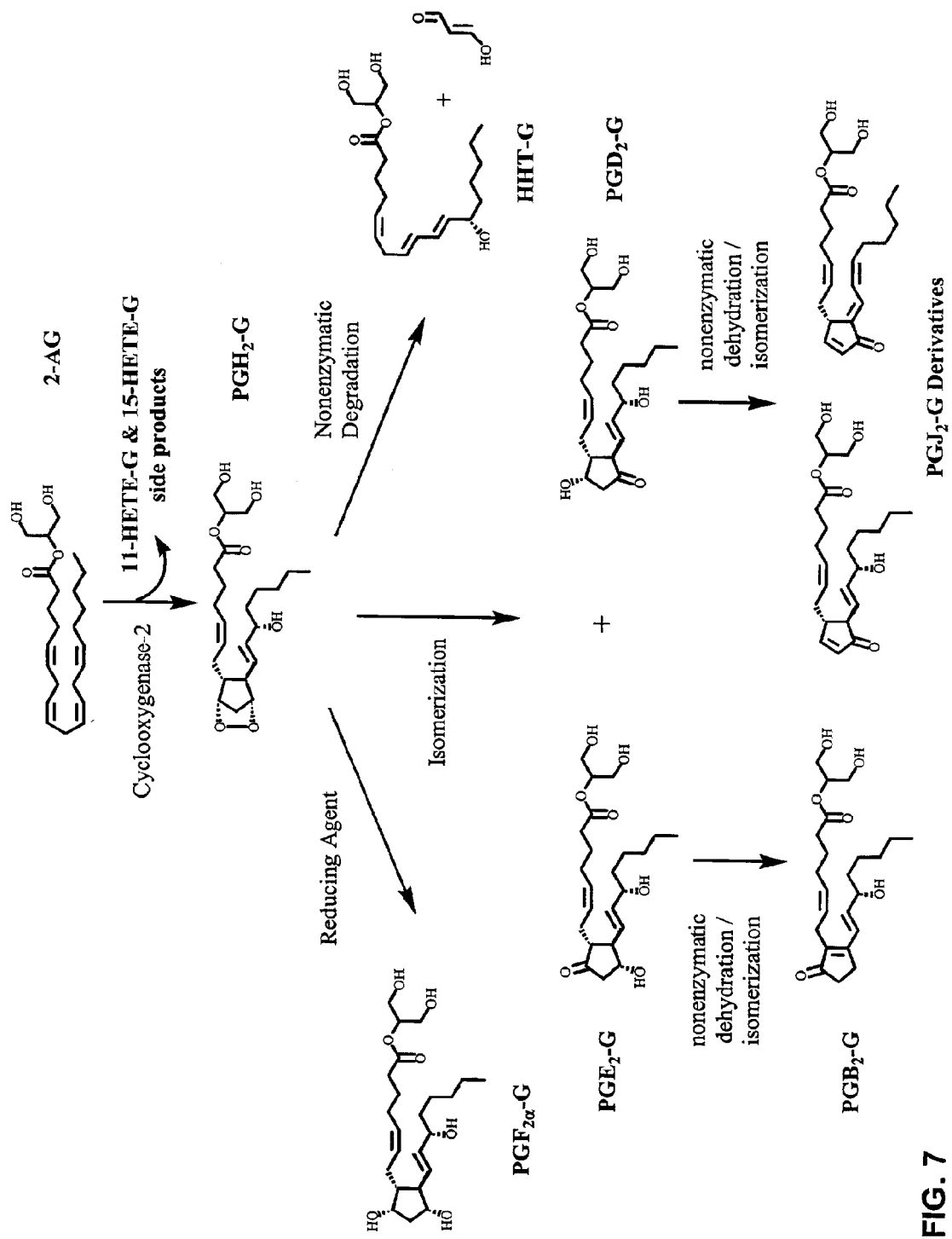
FIG. 7 is a diagram of certain prostaglandin glycerol esters generated following COX-2 action on 2-AG in vitro.
Figure 8:
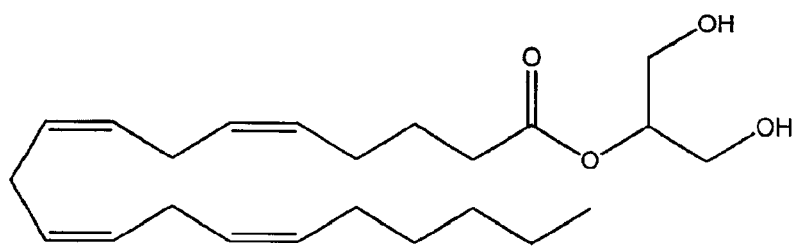
FIG. 8 is a diagram of the structure of 2-arachidonylglycerol (2-AG).

The inventors discovered that 2-AG is present and/or synthesized in vivo (i.e., certain cells in culture and in animals, including in humans and others mammals) and that 2-AG is a COX-2 selective substrate which is transformed by COX-2 to a variety of PG-Gs including those described herein and in FIGS. 5–7. Thus, in certain embodiments, the COX-2 selective metabolite comprises a prostaglandin-glycerol ester (PG-G). A preferred metabolite comprises a 6-keto-prostaglandin F$_{1a}$-glycerol which is derived from PGI$_2$-G (and a product of the activity of COX-2, see FIG. 6). The preferred subject is a human, but other subjects include mammals and other animals in general.

In certain embodiments, the PG-G is PGH$_2$-G, PGE$_2$-G, 15-keto-PGE$_2$-G, 13,14-dihydro-15-keto-PGE$_2$-G, PGD$_2$-G, PGF$_{2a}$-G, TxA$_2$-G, TxB$_2$-B, PGI$_2$-G, 6-keto-PGF$_{1a}$-G, 11-HETE-G, 15-HETE-G, PGA$_2$-G, PGB$_2$-G, and/or HHT-G. Combinations of PG-Gs may be detected in certain embodiments.

In certain embodiments, the ability of COX-1 and/or COX-2 to oxygenate 2-AG is assessed with purified proteins (see Examples 1–4 and FIGS. 9–12; Kozak, K. R., et al. 2000, *J. Biol. Chem.* 275:33744–33749, incorporated herein by reference).

This can be used, for example, to access the relative or absolute COX-2 activity in a subject, system, and/or sample when detecting and/or measuring PG-Gs in the same by techniques including LC/MS or immunoassay.

Detecting and/or measuring COX-2 activity by detecting and/or measuring COX-2 selective metabolites is contemplated in certain embodiments, wherein it is not necessary to obtain a sample or portion of a subject (e.g., certain experimental systems or by using medical scanning techniques).

In another aspect of the present invention, an activity of a COX-2 enzyme is detected by adding a COX-2 selective substrate or a metabolic precursor to a COX-2 selective substrate to a sample (or administering it to a subject). A preferred COX-2 selective substrate comprises 2-AG and a more preferred substrate comprises a labeled 2-AG (e.g., a radio-labeled 2-AG). In certain embodiments, the COX-2 selective metabolites of the labeled 2-AG (or other COX-2 selective substrate) are detected by medical imagining (e.g., PET scan). In certain embodiments, the COX-2 selective metabolites (labeled or unlabeled) are detected by LC/MS or immunoassay.

4.4 Measuring Glyceryl-Prostaglandins

Certain aspects of the present invention provide methods of measuring an activity of a COX-2 enzyme in a subject, system or sample comprising, measuring a metabolite of a COX-2 selective substrate in the subject. The presence of the metabolite in the sample indicates that the COX-2 enzyme is active in the subject. Another aspect comprises a method of measuring an activity of a COX-2 enzyme, comprising measuring an amount of a COX-2 selective metabolite. In certain embodiments, a sample is obtained from the subject and the COX-2 selective metabolite is measured in the sample. The presence of the COX-2 selective metabolite in the sample indicates that there is a COX-2 enzyme activity in the subject. A determination of the amount of the COX-2 selective metabolite in the sample correlates to the level or amount of COX-2 activity in the subject. A preferred COX-2 selective substrate comprises 2-AG. A preferred COX-2 selective metabolite comprises a PG-G. A highly preferred COX-2 selective metabolite comprises a 6-keto-prostaglandin $F_{1\alpha}$-glycerol ester.

In general, measuring means determining the relative or absolute amount of the substance or compound detected. Measurement is generally, but not always, performed relative to a standard. For example, the amount of the standard may be correlated with an amount of COX-2 activity or expression. Therefore, comparing the amount of PG-G measured in a sample from a subject indicates an amount of COX-2 activity in the sample. In certain embodiments, the activity of the COX-2 enzyme determined for the subject can be further related to a level or amount of COX-2 expression in the subject.

PG-Gs and their metabolites may be detected and measured in a variety of ways (see Examples 1–8). In certain embodiments of the present invention, for example, a sample is collected from a subject, and a selective COX-2 substrate, such as 2-AG, is added. Then, a metabolite of the COX-2 selective substrate, such as $PGH_2$-G, is measured. In preferred embodiments downstream metabolites are measured because the half-life of $PGH_2$-G in aqueous solution is approximately 20 seconds. Certain downstream metabolites are more stable and are preferred for measurement. A preferred PG-G for detection and/or measurement is $PGE_2$-G. A highly preferred PG-G for detection and/or measurement is 6-keto-prostaglandin $F_{1\alpha}$-glycerol ester.

In another embodiment of the present invention, both a COX-1 substrate (such as arachidonic acid) and a COX-2 selective substrate (such as 2-AG) can be added to the sample. (It is understood that arachidonic acid is a non-selective COX substrate.) Then the amount of enzymatic metabolite produced from each substrate is measured and compared. In both examples, the samples can be incubated with the substrates over time and a series of measurements of metabolites taken and compared in relation to the amount of time that passed. In certain preferred embodiments of the present invention, no substrate is added to the sample. Instead, the PG-Gs produced from the endogenous 2-AG is detected and measured. In some cases, 2-AG is administered to the subject prior to sample collection, followed by sample collection, and detection and measurement of PG-Gs present in the sample. In preferred embodiments, the amount of PG-Gs measured in the sample is related to an amount of COX-2 activity in the sample or the subject.

Samples from the subject can be processed in several ways (see Examples 7–8). For example, the sample may be extracted at least one time with a solvent, to remove the PG-Gs from the sample for analysis. Extraction can be followed by evaporation. The resulting residue may be redissolved in another solvent and analyzed. This process might involve several rounds of the extraction, evaporation and redissolving steps. Alternatively, the solution resulting from one or more extraction of the sample may be filtered and analyzed. In certain preferred embodiments, the sample is extracted, filtered and analyzed for 2-AG metabolite content.

One aspect of the present invention is a method of detecting COX-2 activity in a biological sample, comprising: incubation of the biological sample with 2-AG, extracting the sample with a solvent, evaporating the solvent to leave a residue and analyzing the residue for PG-Gs wherein the presence of PG-Gs is indicative of COX-2 activity (Example 5). In certain embodiments, the amount of PG-Gs is measured and related to the quantity of COX-2, COX-2 expression, or COX-2 activity. In general, the analysis of PG-Gs includes, but is not limited to, detection by liquid chromatography-coupled mass spectrometry.

Another embodiment of the present invention is a method of detecting COX-2 activity in a biological sample, comprising: extracting PG-Gs present in the sample with a solvent, evaporating the solvent to leave a residue and quantifying PG-Gs in the residue, wherein the presence of PG-Gs is indicative of COX-2 activity. Preferably, the quantity of PG-G detected is related to a quantity of COX-2 activity.

Yet another embodiment of the present invention is a method of detecting and/or measuring a COX-2 activity in a biological sample, comprising: extracting the sample at least one time with a first solvent, evaporating the solvent to leave a residue, dissolving the residue in a second solvent, separating at least one PG-G from the dissolved residue with a separation device, lyophilizing the separated PG-G, dissolving the lyophilized PG-G in a third solvent and detecting dissolved PG-G with a detection device, wherein the presence of the PG-G is indicative of the COX-2 activity (Example 8). In certain embodiments, the amount of PG-G is measured and related to a quantity of COX-2, COX-2 expression, or COX-2 activity. In general, the separation device for separating the PG-G from a residue in the second solvent includes, but is not limited to, a liquid chromatography device.

Yet another aspect of the present invention is a method of detecting and/or measuring COX-2 activity in a biological sample, comprising: extracting at least one PG-G from the sample with a solvent, evaporating the solvent to leave a residue, dissolving the residue in a second solvent, filtering the dissolved residue and detecting a PG-G in the filtered solution with a detection device, wherein the presence of PG-G in the sample is indicative of COX-2 activity. Preferably, the detected glyceryl-prostaglandin is measured and the amount of PG-G measured is related to a quantity of COX-2 activity.

A highly preferred method for detecting and measuring COX-2 selective substrates and COX-2 selective metabolites is LC/MS, the general techniques of which are well known in the art. The application of LC/MS to embodiments of the present disclosure will be readily apparent to one of ordinary skill in the art, in light of the present disclosure.

4.4.1 Use of a Standard

Figure 16:
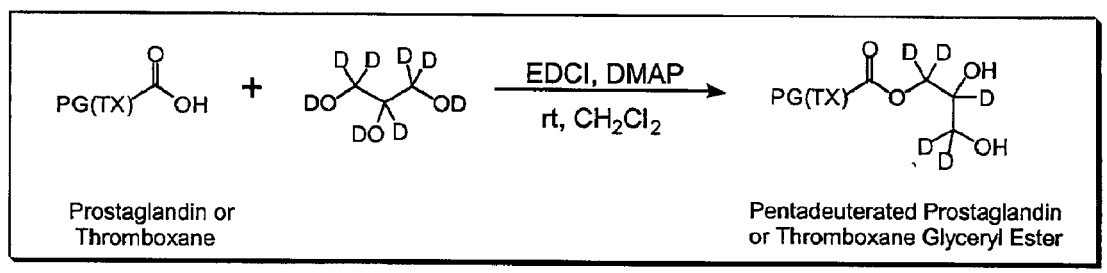
FIG. 16 is a diagram of the general synthesis of pentadeuterated prostaglandin or thromboxane glyceryl ester standards.

In certain embodiments, isotopically labeled PG-Gs are used as an internal standard in quantifying PG-Gs. In certain preferred embodiments, mass spectrometric quantification of PG-Gs is performed. One example of the synthesis of isotopically labeled glycerol esters of prostaglandins and thromboxanes is shown in FIG. 16. In general, isotopically labeled PG-Gs are prepared by coupling the target prostaglandin or thromboxane with anhydrous, isotopically labeled glycerol and purified by chromatography. In addition, labeled standard glyceryl esters of prostaglandins, thromboxanes and their metabolites can be prepared by substituting $^2H$ or $^3H$ for a $^1H$ attached to at least one of the carbons 2–20 of the arachidonyl carbon chain. Alternatively, the PG-G can be labeled by substituting $^{13}C$ or $^{14}C$ for at least one $^{12}C$ in the arachidonyl carbon chain. Labeled PG-Gs can also be made by reacting labeled 2-AG with COX-2, followed by purification of the reaction products. In general, labeled PG-G may also be synthesized by substituting at least one atom in the molecule with an isotope. In certain embodiments, the isotope is positron emitting. In certain embodiments, the isotope is non-positron emitting. Alternatively, the prostaglandin or thromboxane glyceryl esters, or their metabolites can be derivatized to produce chemiluminescent ester standards, which can be used, for example, in an ELISA. In certain embodiments, the standard is used to generate a standard curve, which correlates an amount of signal with a known amount of labeled PG-G standard. The standard curve can be used to determine the amount of PG-G in a sample.

Labeled PG-G standard curves, which correlate with the presence or absence of cancer in a patient, can also be generated. For example, this can be accomplished by collecting samples from groups of patients with different types of cancer, measuring the amount of glyceryl-prostaglandins in the samples, and graphing the amounts of PG-Gs versus the types, stages, and/or grades of cancer. In certain embodiments, types of cancer can be varieties of cancer. In preferred embodiments, the types of cancer are a range of particular cancers measured on a clinical scale of severity or aggressiveness (i.e., stage or grade). Such a standard curve may also indicate that the cancer stage or grade correlates with the amount of PG-G found in the sample. In addition, since small amounts of PG-Gs can be found in samples collected from people without cancer, a threshold level of PG-Gs will be observed at which amounts of PG-Gs below the threshold will correlate with the lack of cancer in the patient. On the other hand, for example, amounts of PG-Gs measured in a sample that are above the threshold level correlate with the presence of cancer in the patient.

In a similar example, a standard curve can be developed which correlates the amount of PG-G observed in a sample from a patient with an amount of inflammation. Such a standard curve can be generated by collecting samples from a patient population suffering from inflammatory processes, and correlating the amount of PG-G in the samples with the severity of disease of the patients.

In another example, no standard or standard curve is used. Instead, a series of samples may be collected from a single patient over a period of time, and the amount of PG-G in each sample measured. Then the amounts of PG-G measured would be compared and correlated with the amount of time which had passed between sample collections. If the amount of PG-G in the samples increased over time, for example, this would indicate that the patient's disease process is progressing, or that therapy that the patient might be receiving isn't working. On the other hand, if the amount of PG-G measured in the samples decreased over time, for example, this would indicate that the patient's disease process is slowing, stopping or improving, or that the therapy that the patient might be receiving is working.

4.4.2 Detection and Measuring Device

In general, a detection device for detecting PG-Gs or their metabolites includes, but is not limited to, a mass spectrometer, a chromatography-coupled mass spectrometer, an immunoassay or an enzyme-linked immunoassay, or other means for detecting PG-Gs known in the art (see Examples 2–6). In certain embodiments of the present invention, liquid chromatography/mass spectrometry (LC/MS) is conducted, preferably with a Waters 2690 Separations Module with a Zorbax RX-C18 narrow bore column (15 cm×2.1 mm, 5 μm) interfaced to a Finnigan TSQ-7000 triple quadrupole mass spectrometer. Sodiated analytes are eluted with increasing concentrations of MeCN in 0.001% aqueous NaOAc. Evaluation of PG-Gs or their metabolites in biological samples is conducted with selected ion monitoring and quantification is accomplished using pentadeuterated PG-G standards.

4.4.3 Separation Device

A variety of separation devices known in the art for separating prostaglandins from a sample may be used. In general, separation devices include, but are not limited to, extraction columns, affinity columns, filters, thin-layer chromatography plates and gels.

In certain embodiments of the present invention, a PG-G in a sample may be isolated or purified (separated partially or substantially from the natural constituents of a PG-G containing sample) using one or more techniques known in the art for the separation of chemical and especially prostaglandin compounds, for example, but not limited to, liquid chromatography.

4.4.4 Subjects

In certain embodiments of the present invention, the subject includes a mammal, such as a rodent, preferably a human, or a cultured cell of a mammal, including a cultured cell of a human. In general, the subject is any animal, laboratory specimen, cell culture, tissue, etc. Other subjects include farm animals and show animals (horses, cattle, sheep, pigs and swine, goats, fowl, and the like), pets (dogs, cats, parrots, canaries and the like), animals kept in zoos and endangered species (elephants, lions, tigers, antelope, zebra, anteaters, water buffalo, pandas, cheetahs, kangaroos, ostriches, eagles, condors, finches, and the like) or a cultured cell of said animal.

4.4.5 Samples

In certain embodiments, the sample is urine, blood, plasma, cerebrospinal fluid, saliva, sputum, bile, joint fluid, or biopsy, or may be collected from or processed from one or more of these fluids and tissues. In further embodiments of the present invention, the sample may be conditioned media from a cell culture.

In certain embodiments, the sample is urine or may be collected from or processed from urine (Example 7). For example, the sample of urine may be collected by having the subject urinate in a cup. PG-Gs and their metabolites can be measured in urine by isotope dilution mass spectrometry.

Figure 17:
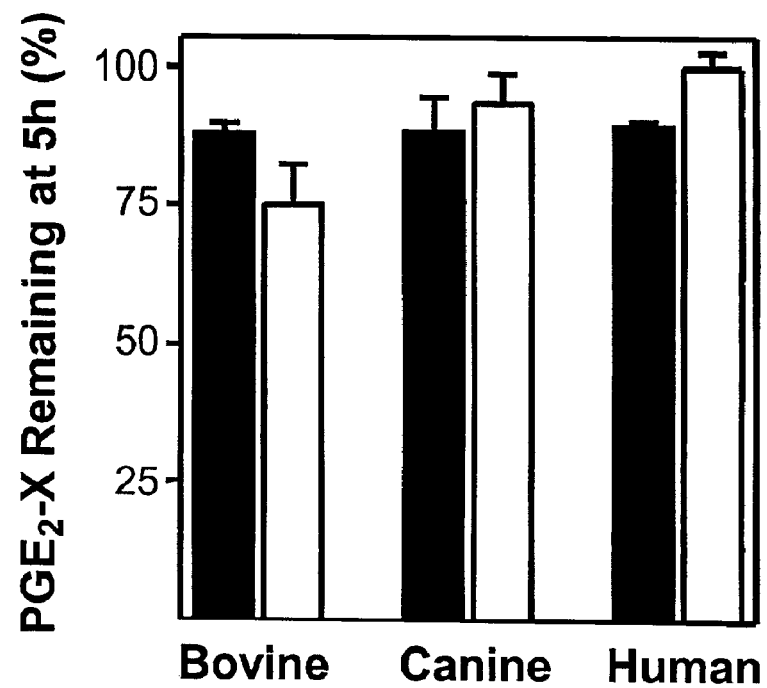
FIG. 17 is a graph showing the stability of PGE$_2$-G in bovine, human, and canine cerebrospinal fluid (CSF).
Figure 18:
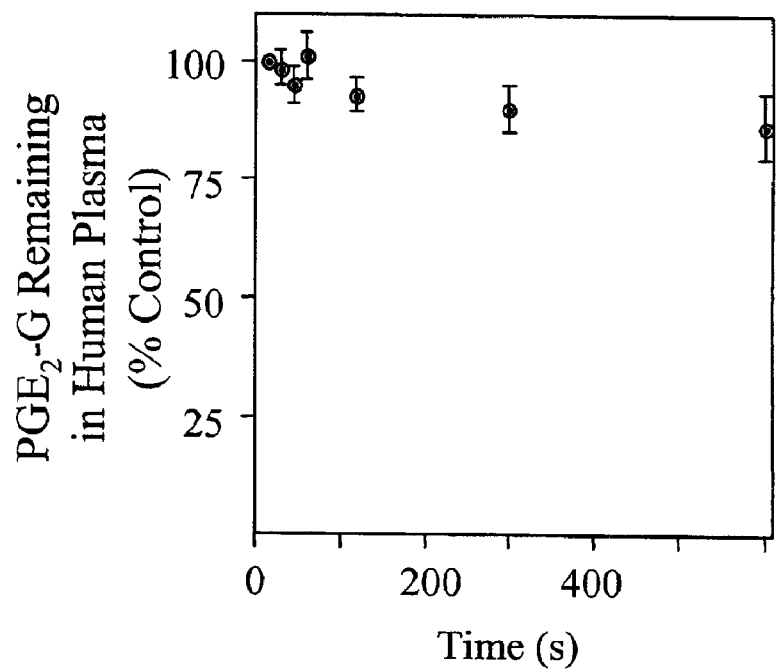
FIG. 18 is a graph showing the stability of PGE$_2$-G in human plasma.

Certain PG-Gs and their metabolites are stable in cell culture (FIGS. 13–14); human, bovine, and canine CSF (FIG. 17); and human plasma (FIG. 18). In certain embodiments, the sample is blood, plasma, cerebrospinal fluid, saliva, sputum, bile, joint fluid, biopsy, immune cells, cancer cells, tumor cells, malignant cells, inflammatory cells, non-tumor cells, non-immune cells, cells not activated by inflammatory stimuli or may be collected from or processed from one or more of these fluids and tissues. For example, blood may be aseptically collected from the subject with a needle inserted into a vein. The blood may then be treated in standard ways to separate the plasma, and then the PG-Gs are extracted from the plasma or the cell fraction separated from the blood. In certain embodiments of the present invention, the sample may be conditioned media collected from a cell culture or cell lysate prepared from cultured cells (Example 8). In certain embodiments of the present invention, a plurality of samples may be collected from the subject, with a period of time being allowed to pass between consecutive collections of the samples. The amounts of PG-Gs or their metabolites present in these samples are measured, compared and related to the periods of time that had been allowed to pass. In certain embodiments, the subject is a patient and the samples are taken in order to evaluate the effectiveness of anti-cancer therapy and to evaluate tumor stage or grade.

4.4.6 Antibody Synthesis

Monoclonal and polyclonal antibodies to PG-Gs or their metabolites can be made using standard antibody generation techniques, in light of the present invention (Cohen, et al., U.S. Pat. No. 5,589,575, herein incorporated by reference; McCafferty, et al. 1996, *Antibody Engineering, a Practical Approach*, IRL Press; Mernaugh & Mernaugh 1994, *Methods for the Production of Monoclonal Antibodies*, in Molecular Methods in Plant Pathology). For example, monoclonal antibodies against $PGE_2$ are commercially available from Cayman Chemical (118 E. Ellsworth Rd., Ann Arbor, Mich. 48108, 800-364-9897) and chemiluminescent ELISA kits for several PGs, HETE and $TxB_2$ are available from Assay Designs, Inc. (800 Technology Dr., Ann Arbor, Mich. 48108; 734-668-6113). To create antibodies that recognize $PGE_2$-G, for example, the cyclopentyl substituents and ester moiety of the $PGE_2$-G are protected using standard techniques. Then the protected $PGE_2$-G is covalently modified with an appropriate conjugate (e.g., KLH) using standard techniques known to one skilled in the art in light of the present invention (references supra). After completion of haptenization, the haptenized molecules are deprotected and used to inoculate mice, rabbits or goats, using standard techniques. According to standard protocols, serum would be collected from inoculated animals and antibodies are purified from the serum. Alternate approaches to antibody development known in the art can also be employed using the immunogen described above and in light of the present invention.

4.5 COX-2 and Inflammatory Diseases/Disorders

A variety of human diseases are associated with inflammation. These include, but are not limited to: acute appendicitis, asthma, myocardial infarction, specific immunological disease processes, infection with viruses or bacteria, endotoxemia and reperfusion injury. Certain aspects of the present invention provide novel and useful compositions, methods and articles of manufacture for diagnosing or monitoring an inflammatory disease state in a patient by detecting and measuring COX-2 activity in a sample of the patient (Example 9). The present invention is also useful in detecting and treating non-malignant or immunological-related cell-proliferative diseases such as psoriasis, pemphigus vulgaris, Behcet's syndrome, acute respiratory distress syndrome (ARDS), ischemic heart disease, post-dialysis syndrome, leukemia, acquired immune deficiency syndrome, septic shock and other types of acute and chronic inflammation, and lipid histiocytosis.

In certain aspects of the present invention, a sample is collected from a patient suspected of having an inflammatory disease or diagnosed with an inflammatory disease, such as arthritis, and a PG-G in the sample is detected and measured. The amount of PG-G measured is indicative of COX-2 activity in the patient and the level of COX-2 activity may be used by the attending physician as a marker of the progress or severity of the inflammatory disease process.

In further aspects of the present invention, a series of samples may be collected over a period of time from the patient suspected of having or diagnosed with an inflammatory disease. During the period of time during which samples are collected, the patient may undergo therapy for the inflammatory disease. The amount of PG-G in each sample would be measured and correlated with COX-2 activity in the patient. The amount of COX-2 activity in the patient is correlated with the amount of inflammation in the patient. Changes in the amount of COX-2 activity would be used by the physician to evaluate the patient's condition as well as the effectiveness of the therapy being used to treat the patient's inflammatory disease, wherein a decrease in PG-G or COX-2 activity is indicative of an improvement in the patient's condition or of effective therapy.

4.6 COX-2 and Cancer

Studies in human colon cancer have shown that COX-2 expression is increased in colon cancer cells compared to the adjacent colonic mucosa; similar observations have been made in experimental models of colon cancer (Eberhart, C E, et al. 1994, *Gastroenterology* 107:1183; Sheng, H, et al. 1997, *J. Clin. Invest.* 99:2254; DuBois, R N, et al. 1996, *Gastroenterology* 110:1259). COX-2 expression is a marker for the metastatic potential of colon cancer cells and is related to patient survival (Tsujii, M, et al. 1997, *Proc. Natl. Acad. Sci. USA* 94:3336; Sheehan, K M, et al. 1999, *JAMA* 282:1254). In one study, for example, COX-2 expression was determined in 76 patients with a variety of stages of colorectal cancer (Sheehan, K M, et al., 1999, *JAMA;* 282:1254). Ten-year survival was significantly higher in patients with the lowest levels of COX-2 expression (68 versus 35 percent). Such studies can be used to generate a standard curve for PG-G production and cancer, especially in colon cancer (see supra). These findings suggest that COX-2 activation promotes tumor growth. Consistent with this hypothesis is a study in which human colon cancer cells that expressed high levels of COX-2 were implanted into nude mice. Treatment with a selective COX-2 inhibitor reduced tumor formation by 85 to 90 percent and inhibited colony formation of cultured cells (Sheng, H, et al. 1997, *J. Clin. Invest.* 99:2254). This benefit was not seen with tumor cells that lacked COX-2.

In certain aspects of the present invention, samples may be collected from a patient suspected of having a tumor (Example 10). The amount of PG-G would be detected and/or measured, and is indicative of COX-2 activity in the patient. COX-2 activity can be used as a marker for the presence of the tumor in the patient by the patient's physician. More preferably, an amount of PG-G detected in the sample of the patient will be measured, wherein the amount of PG-G measured is indicative of the type, stage, and/or grade of tumor present in the patient.

A further aspect of the present invention is a method of monitoring anticancer therapy effectiveness. In general, a series of samples are collected from the patient over a period of time. This period of time might be, for example, a few days, weeks or even months. During this period of time, the patient may undergo anticancer therapy. The amounts of PG-G in the samples are measured and correlated with the amounts of time allowed to pass between the collections of the samples. Increases in the amounts of PG-G measured are indicative of increased tumor growth, which can include increases in the size of a single tumor or multiple tumors, or increases in the number of tumors present. This may be interpreted, preferably by the physician, as failure of the anticancer therapy. Decreases in the amounts of PG-G measured are indicative of decrease in tumor size or number. This may be interpreted by the physician as success of the therapy. In certain aspects of the present invention, samples may be collected from a patient in remission. The level of PG-G would be determined in order to monitor for the recurrence of the cancer. Levels of PG-G above a threshold value would be indicative of cancer recurrence.

In general, the effectiveness of the cancer therapy is evaluated based on the changes in the amount of sample PG-G observed over time. For example, increases in the amount of PG-G over time indicate continued tumor growth and the failure of anti-cancer therapy; whereas decreases in the amount of PG-G over time are indicative of therapy success and tumor regression. In certain embodiments of the present invention, the sample is a culture of cancer cells used as an experimental model, a culture of cancer cells taken from a patient, or a biopsy sample of tissue. The cancer cells may be treated with an anti-cancer therapy in vitro in order to evaluate the effectiveness of that therapy in relation to alternative cancer therapies. In certain embodiments, this procedure is done in order to determine an optimal anti-cancer therapy for that individual patient.

In certain embodiments, the attending health professional may characterize both an inflammatory process and a malignancy in the subject by detecting and measuring an amount of a PG-Gs in a sample of a subject specifically produced by the offending malignancy and inflammatory lesion.

4.7 COX-2 and Research

In the prior art, investigations which attempt to identify links between COX-2 expression/activity and disease processes are time- and labor-intensive and often require examination of tissue samples post-mortem. For example, attempts to study the role of COX-2 in Alzheimer's disease (AD) require post-mortem collection of brain tissue from both deceased AD and control subjects and quantitative assessment of COX-2 expression in this tissue using standard biochemical techniques (e.g., Western blotting). Such studies are also hampered by the inability to assess enzyme activity, which may or may not correlate with enzyme expression. The use of PG-G quantification in this setting allows for a relatively non-invasive quantification of COX-2 activity in vivo. This technique provides at least two fundamental benefits. First, the noninvasive nature allows for much broader testing increasing the sample size in these studies and permitting rapid and statistically significant association (or lack thereof) between COX-2 and the pathology under study. Second, given the possibility of testing patients before disease signs are evident will allow for assessing the role of COX-2 in disease development and progression in contrast to post-mortem studies which evaluate the role of COX-2 long after the disease process begins. Quantification of PG-Gs in vivo provides a simple assay for assessing the in vivo efficacy of newly developed COX-2 inhibitors.

In addition, there is a great need to discover and develop new COX-2 specific regulators. However, current methods are time and labor intensive. The present invention provides compositions, methods and kits for screening candidate molecules for their ability to regulate COX-2 using purified COX-2, tissue culture, or an animal model (Examples 11–12).

4.8 Kits

Certain embodiments of the present invention provide an article of manufacture for the detection and/or measurement of COX-2 activity by the detection and/or measurement of PG-Gs or their metabolites by immunoassay (including ELISA, radioimmunoassay, etc.), comprising an antibody to the COX-2 selective metabolite. In certain embodiments, the kit further comprises a set of instructions delineating a process for relating a detection and/or measurement of PG-Gs and their metabolites in a sample to a detection and/or measurement of COX-2 in a subject or a sample thereof. Preferably, the article of manufacture comprises an antibody against PG-Gs or their metabolites. More preferably, the article of manufacture further comprises one or more of the standard reagents required to perform an immunoassay, such as buffers, multi-well plates, additional antibodies and the like. Still more preferably, the article of manufacture further comprises one or more boron-based solid phase extraction columns for isolation of PG-Gs and their metabolites from prostaglandin free acids. Preferably, the article of manufacture further comprises a set of standards, such as pentatritiated $PGE_2$-G. In certain embodiments, the article of manufacture comprises a standard suitable for dilution mass-spectroscopy and a set of instructions for performing the dilution mass-spectroscopy. More preferably, the article of manufacture further comprises an unlabeled PG-G internal standard for standard curve development.

In certain embodiments, the article of manufacture comprises a vial containing a labeled PG-G for use as a detection/measurement standard.

In further embodiments the present invention provides an article of manufacture for the detection and/or measurement of COX-2 activity by mass spectrometry, which comprises: a set of instructions delineating a process for relating a detection and/or measurement of PG-Gs in a sample to a detection and/or measurement of COX-2 in a subject or a sample thereof and a C18 solid phase extraction column. Preferably, the article of manufacture further comprises a set of standards. More preferably, the article of manufacture further comprises an unlabeled PG-G positive control, and a pentadeuterated or pentatritiated PG-G internal standard.

Another aspect of the present invention is an article of manufacture comprising packaged together a vessel containing purified PG-G and a set of instructions for use of the PG-G for the evaluation of COX-2 activity in a biological sample. Other kit components may include an anti-PG-G antibody or a single chain fraction variable portion of such an antibody. An anti-PG-G antibody would be labeled to facilitate detection. Such a label would be, but is not limited to, nonpositron-emitting isotopes, such as deuterium and tritium, and chemiluminescent or fluorescent compounds.

4.9 Certain Novel PG-Gs

Referring to FIG. 21, the novel compound 6-keto-prostaglandin $F_{1\alpha}$-glycerol ester (6-keto-$PGF_{1\alpha}$-G) is confirmed by selected-ion mass chromatography (m/z=467, top panel; m/z=472 bottom panel) of the enzymatic product resulting from the sequential actions of COX-2 and PGIS on 2-AG (top panel) and the synthetic product of EDCI-mediated coupling of 6-keto-$PGF_{1\alpha}$ and deuterated glycerol (bottom panel). Products were eluted with a 15 minute gradient of 20–100% acetonitrile in $H_2O$ (0.001% sodium acetate). The present invention provides novel compounds including, but not limited to: $PGI_2$-G, 6-keto-$PGF_{1\alpha}$-G, and isotopically labeled $PGI_2$-G and 6-keto-$PGF_{1\alpha}$-G. Although the $PGI_2$-G was not directly detected in the experiments performed, it is a necessary intermediate for the production of 6-keto-$PGF_{1\alpha}$-G by the action of COX-2 and PGIS.

In certain embodiments, isotopically labeled 6-keto-$PGF_{1\alpha}$-G is manufactured from the coupling of 6-keto-$PGF_{1\alpha}$ and isotopically labeled glycerol. In certain embodiments, isotopically labeled $PGI_2$-G and 6-keto-$PGF_{1\alpha}$-G are manufactured by the sequential reaction of COX-2 and PGIS with isotopically labeled 2-AG. (Isotopically labeled 2-AG is available from Cayman Chemical, U.S.A.).

5.0 EXAMPLES

The present invention is further illustrated by the following specific examples. The examples are provided for illustration only and are not to be construed as limiting the scope or content of the invention in any way.

5.1 Example 1

Figure 9:
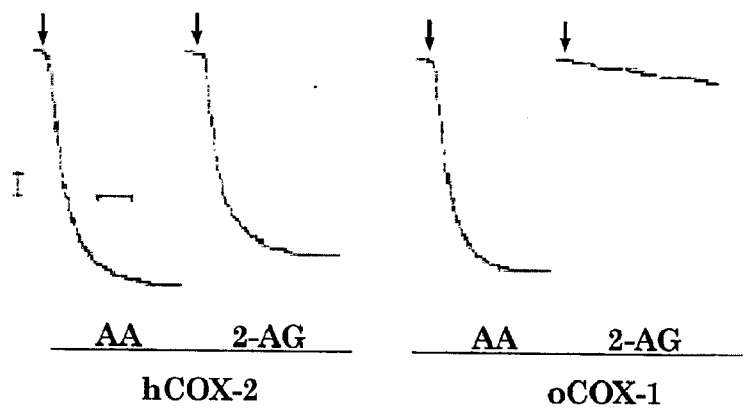
FIG. 9 is an oxygen uptake plot for human COX-2 and ovine COX-1 incubated with arachidonic acid or 2-AG.

The ability of COX-1 and COX-2 to metabolize different substrates, such as 2-AG and arachidonic acid (AA) can be determined, for example, by measuring relative oxygen uptake. FIG. 9 is a representative oxygen uptake curve for 100 μM 2-AG or AA treated with 150 nM purified COX-2 or 150 nM ovine COX-1. The horizontal bar represents 20-seconds. The vertical bar represents 10 μM $O_2$ uptake. Incubation of 2-AG with purified human COX-2 triggers $O_2$ uptake comparable in rate and extent to that observed with arachidonic acid ($O_2$ is a reactant in the process). In contrast, relatively little O₂ uptake is observed following addition of ovine COX-1 to 2-AG. Steady state kinetic analysis of COX-2-mediated 2-AG oxygenation reveals that both the human and murine enzymes display apparent $k_{cat}/K_M$ values similar to those determined for arachidonic acid (see TABLE 1). TABLE 1. Steady-state kinetic parameters for COX-2 mediated 2-AG and AA oxygenation.

TABLE 1

Steady-state kinetic parameters for COX-2 mediated 2-AG and AA oxygenation.

| Enzyme | Substrate | $k_{cat}$ (s⁻¹) | $K_M$ (μM) | $k_{cat}/K_M$ (s⁻¹μM⁻¹) |
|---|---|---|---|---|
| hCOX-2 | AA | 14.7 ± 0.5 | 6.1 ± 0.6 | 2.4 |
|  | 2-AG | 17.4 ± 1.1 | 4.4 ± 0.9 | 4.0 |
| mCOX-2 | AA | 20.5 ± 1.6 | 8.2 ± 1.6 | 2.5 |
|  | 2-AG | 11.1 ± 0.7 | 4.7 ± 0.8 | 2.3 |

Figure 10:
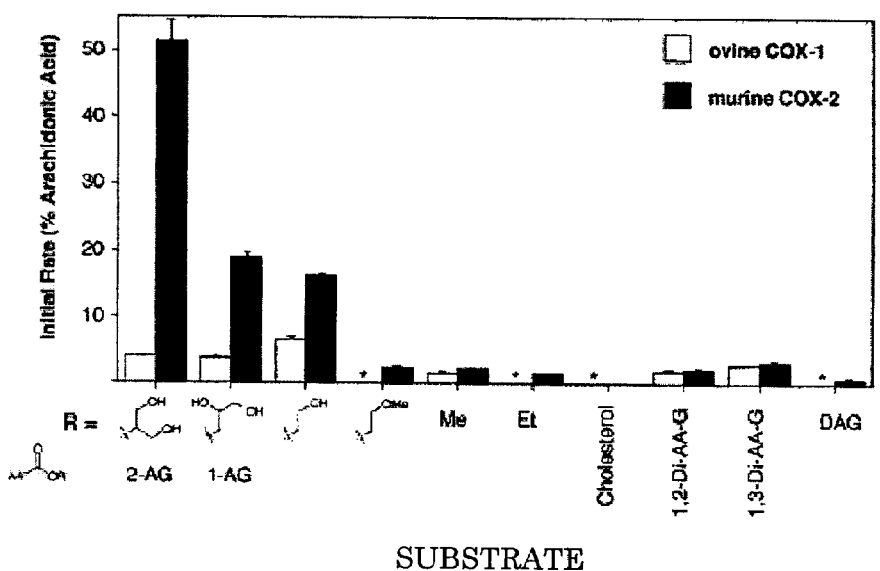
FIG. 10 is a graph of oxygen uptake rates for COX-2 and COX-1 using different arachidonylester substrates.

Among a series of arachidonyl esters, 2-AG is the preferred substrate of COX-2 (see FIG. 10; Kozak et al. 2000, supra). FIG. 10 is a graph of the specificity of arachidonyl ester substrates. Initial O₂ uptake rates of arachidonyl esters (200 μM) by murine COX-2 (200 nM) and ovine COX-1 (150 nM) are shown and normalized to the rate of O₂ uptake for arachidonic acid (AA, 100 μM) (mean±SEM, n≧3). The asterisks indicates a substrate that is not evaluated with COX-1. DAG stands for diacylglycerol and Di-AA-G stands for diarachidonylglycerol. Of particular interest, COX-2 oxygenates 2-AG (bar 2) at a dramatically higher rate than COX-1 (bar 1).

5.2 Example 2

Figure 11:
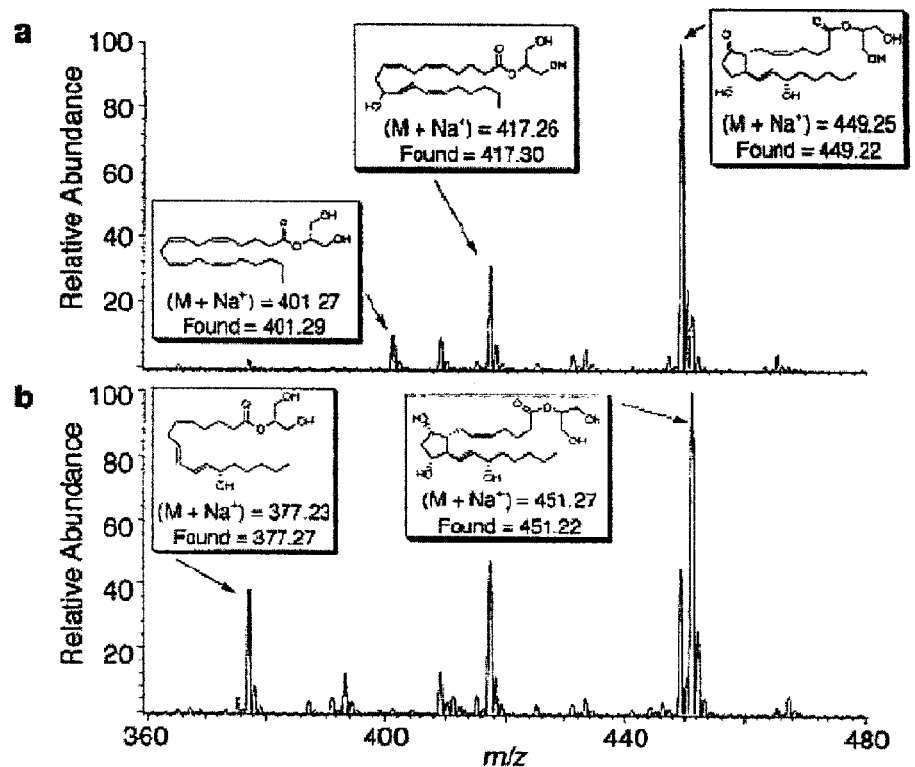
FIG. 11 is a diagram of mass spectra of oxygenated 2-AG products.

The products of metabolism of 2-AG by COX-2 can be identified, for example, by mass spectrometry. FIG. 11 is a mass spectrogram of oxygenated 2-AG products. Representative direct liquid infusion, positive ion, electrospray ionization mass spectra of 2-AG metabolites is obtained by treating 15 ng 2-AG with (a) 15 μg purified human COX-2 for 2-minutes at 37° C., or (b) 30 μg purified human COX-2 for 2-minutes at 37° C. This is followed by reduction with 15% Na₂S₂O₄ for 20-minutes at room temperature. Chemical structures indicate the assignment for the most abundant product with the appropriate mass-to-charge ratio. Electrospray ionization mass spectrometric analysis of an extract of a reaction mixture directly infused into the spectrometer reveals two primary product masses at m/z 449 and 417, which correspond to the sodiated molecular ions of the glyceryl esters of PGH₂, PGE₂, or PGD₂ and 11- or 15-(HETE), respectively (FIG. 11a). The presence of sodium in the molecular ions is confirmed by collision-induced dissociation. Treatment of 2-AG/COX-2 incubation mixtures with endoperoxide reducing agents (triphenylphosphine, SnCl₂ or Na₂S₂O₄) results in the disappearance of the ion at m/z 449 and the appearance of a product with a molecular ion at m/z 451 (FIG. 11b). This is consistent with reduction of PGH₂-G to PGF₂-G.

5.3 Example 3

Figure 12:
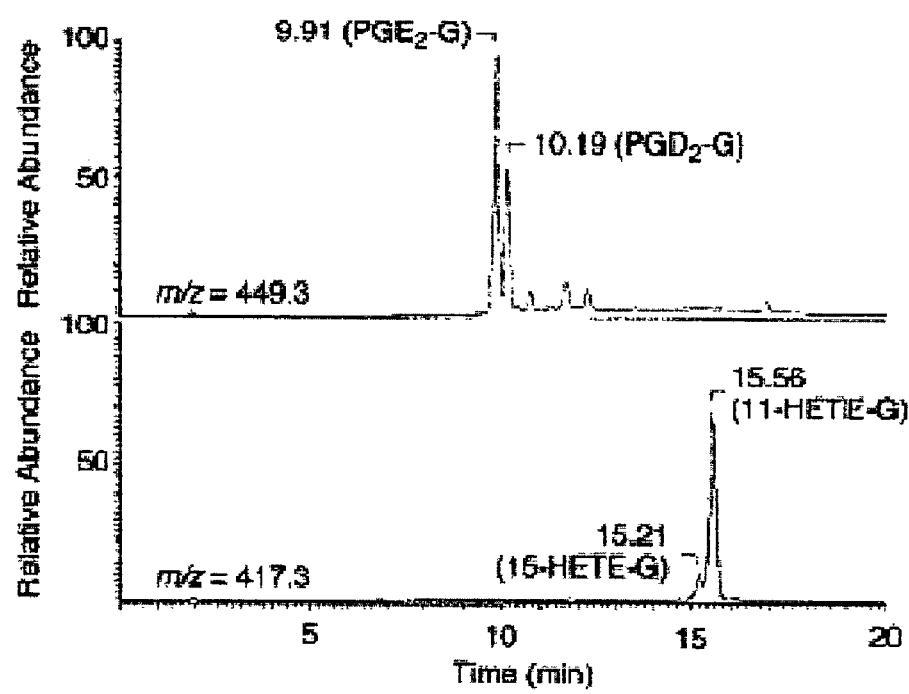
FIG. 12 is a reversed phase liquid chromatography mass spectrometry selected-ion chromatogram of oxygenated 2-AG metabolites.

In general, COX-2 enzymatic products can be detected or measured by a variety of methods. For example, reversed phase liquid chromatography-mass spectrometry is used to detect or measure COX-2 enzymatic produces. FIG. 12 is a selected-ion mass chromatogram of oxygenated 2-AG metabolites with (a) m/z=449.3 and (b) m/z=417.3 (Kozak et al. 2000, supra). For example, products are eluted with a 15-minute gradient of 20% to 100% acetonitrile in H₂O (0.001% sodium acetate). LC/MS reveals the presence of five primary products in 2-AG/COX-2 reaction mixtures. Two closely eluting polar products each display m/z 449 consistent with the non-enzymatic PGH₂-G isomerization products PGE₂-G and PGD₂-G (FIG. 12). Pentadeuterated standards of glyceryl esters of PGE₂ and PGD₂ are synthesized and coelute with these two polar products under multiple chromatographic conditions. An intermediate polarity product with m/z 377 is observed that is consistent with the PGH₂-G degradation product 12-hydroxyheptadeca-5,8,10-trienoic acid (HHT-G, data not shown). Finally, two closely eluting non-polar 2-AG metabolites are detected with an m/z of 417, consistent with the glyceryl esters of HETEs (hydroxyeicosatetraenoic acids that are minor products of arachidonic acid oxygenation by COX-2) (FIG. 12).

5.4 Example 4

Estimates of relative amounts of the individual PG-Gs can be made by reversed-phase HPLC with UV detection. The two polar PG-Gs exhibit no significant absorption above 215 nm, indicating the absence of a conjugated diene functionality, whereas both the intermediate polarity PG-G and the two non-polar PG-Gs exhibit absorption maxima near 235 nm, consistent with the presence of a conjugated diene. Base treatment of the oxygenated 2-AG metabolites affords free acids that coelute with standards of 15- and 11-HETE and the PGE₂ dehydration/isomerization product, PGB₂ which displays an absorption maximum at 278 nm. Quantification of PGE₂-G and HETE-Gs is accomplished by HPLC/UV analysis of base-treated COX-2/2-AG incubation mixtures using 5-HETE as an internal standard. PGE₂-G is the major product of oxygenation (PGE₂-G/HETE-G= 4.0±0.1, n=5) and 11-HETE-G is more abundant than 15-HETE-G (11-HETE-G/15-HETE-G=3.4±0.1, n=5). HETE-G regiochemistry is confirmed by mass spectrometry of saponified, HPLC-purified HETE products.

5.5 Example 5

Figure 13:
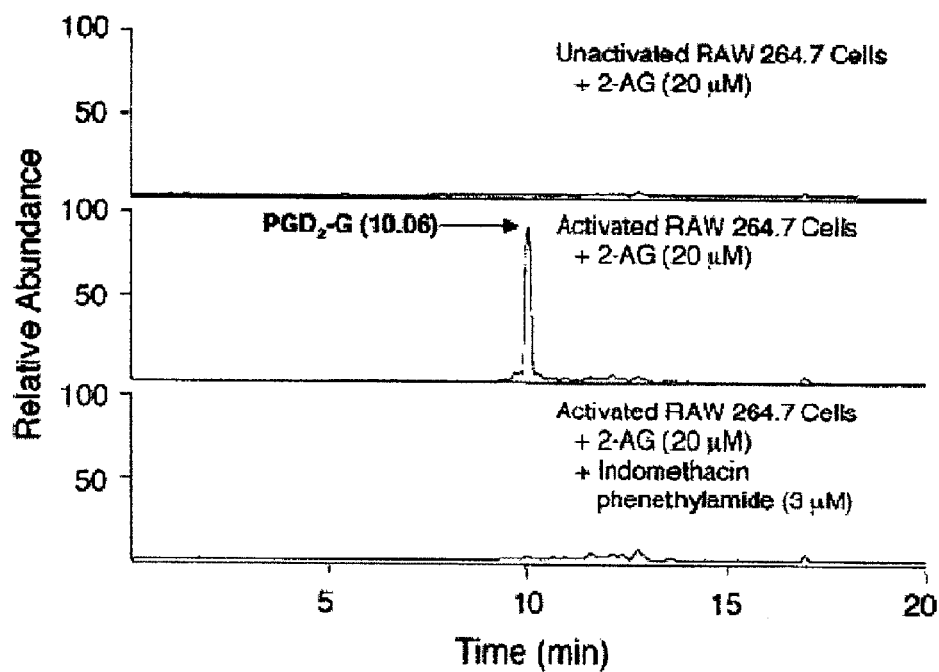
FIG. 13 is a reversed phase liquid chromatography mass spectrometry selected-ion chromatogram showing oxygenated 2-AG metabolites from activated RAW264.7 cells exposed to 20 µM 2-AG.

Cellular COX-2 enzymatic activity can be determined by exposing cells to exogenous 2-AG and measuring the COX-2 specific products. For example, unactivated RAW264.7 cells (a murine macrophage cell line) express no detectable COX-2 and low levels of COX-1, but IFN-γ and LPS induce COX-2 expression (Wadleigh, D. J. et al, 2000, J. Biol. Chem. 275:6259–6266). The major arachidonic acid metabolite in these cells is PGD₂, so RAW264.7 cells permit the simultaneous evaluation of 2-AG oxygenation to PGH₂-G as well as endoperoxide metabolism by PGD synthase (Landino, L. M., Crews, B. C., Timmons, M. D. et al., 1996, Proc. Natl. Acad. Sci. USA 93:15069–15074). Glyceryl prostaglandins are not detectable in the medium from unactivated RAW264.7 cells following addition of a physiologically relevant concentration of 2-AG (20 μM) (Kozak et al. 2000, supra). However, treating cells with LPS (1 μg/mL) and IFN-γ (10 units/mL) results in the synthesis and release of copious amounts of PGD₂-G, following the addition of 2-AG (20 μM). FIG. 13 is a LC/MS chromatogram showing the PGD₂-G production and extracellular release by activated RAW264.7 macrophages. Products are eluted with a 15-minute gradient of 20% to 100% acetonitrile in H₂O (0.001% sodium acetate). Chromatograms are normalized to total ion current of 2-AG- treated activated macrophages. PGD₂-G biosynthesis is inhibited both by indomethacin (3 μM) and the highly selective COX-2 inhibitor, 2-[1-(4-chlorobenzoyl)-5-methoxy-2-methyl-1H- indol-3-yl]-N-phenethylacetamide (indomethacin phenethylamide, 3 µM). No significant endogenous PGD$_2$-G biosynthesis is detected in the absence of exogenous substrate under these conditions (FIG. 13 and data not shown).

5.6 Example 6

Figure 14:
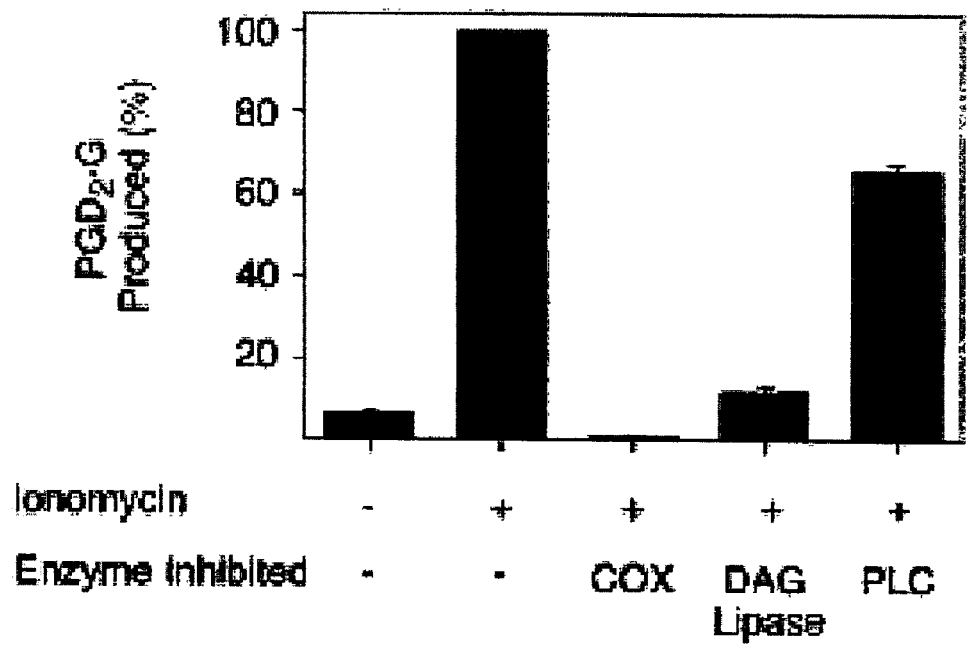
FIG. 14 is a graph showing endogenous PGD$_2$-G production and extracellular release by ionomycin-stimulated, activated macrophages.

Cellular COX-2 enzymatic activity can be determined by measuring the COX-2 specific products produced from endogenous 2-AG. For example, FIG. 14 shows the endogenous PGD$_2$-G production and extracellular release by ionomycin-stimulated, activated macrophages. Inhibitors are added 20 minutes prior to ionophore addition as the concentrations indicated below. Values are normalized to PGD$_2$-G production by uninhibited macrophages and represent the mean±SEM (n=6, P<0.001). Product identification is accomplished by coelution under multiple chromatographic conditions of macrophage product with both pentadeuterated PGD$_2$-G and the minor m/z 449 species produced by incubating 2-AG with purified COX-2. Ionomycin stimulation (5 µM) of IFN-γ/LPS-activated RAW264.7 cells results in the production and extracellular release of PGD$_2$-G (FIG. 14). Quantification of PGD$_2$-G using a pentadeuterated standard reveals 7.0±0.1 ng PGD$_2$-G released per 10$^6$ cells (mean±SEM, n=9).

5.7 Example 7

Figure 15:
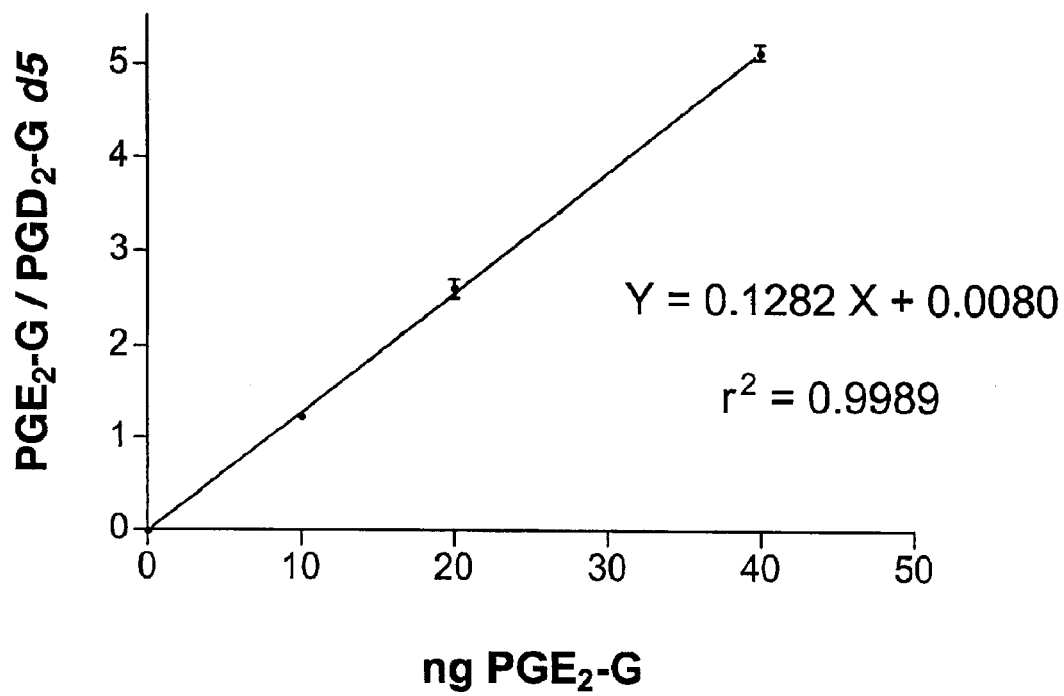
FIG. 15 is a graph of recovery of glyceryl prostaglandins in human urine by C18 solid phase extraction chromatography.

A sample may be urine or may be collected from or processed from urine. Glyceryl prostaglandins can be measured in urine by isotope dilution mass spectrometry. A fixed volume of urine is treated with an appropriate internal standard (e.g. pentadeuterated glyceryl prostaglandin) and then loaded on reversed-phase extraction cartridges. The sample is then washed (e.g. 1 ml pH 4.0 20 mM NaOAc) and glyceryl prostaglandins or their metabolites including the added internal standard are eluted with organic solvent (e.g. two 1 ml aliquots of MeCN). The solvent is evaporated and the residue is analyzed by LC/MS. A typical procedure wherein synthetically generated PGE$_2$-G and d5-PGD$_2$-G is added to fresh human urine is depicted in FIG. 15 and demonstrates that this technique provides precise and linear quantitation over the tested range (0–40 ng PGE$_2$-G per ml urine).

5.8 Example 8

Samples can be collected from or prepared from cultured cells. A variety of cells lines known to one skilled in the art are acceptable. In addition, primary cell cultures can be used. Methods for collecting and culturing primary cell cultures are well known in the art. For example, exogenous 2-AG metabolism by RAW264.7 cells can be measured. Low passage number murine RAW264.7 cells are grown in DMEM containing 10% FBS. Cell activation is performed as described in the art (Landino, L. M., et al. 1996, *Proc. Natl. Acad. Sci. USA* 93: 15069–15074). Briefly, macrophages (30–50% confluence) are activated with IFN-γ (10 units/mL) and LPS (1 µg/mL) in serum-free DMEM for 7 hr at 37° C. prior to treatment. Activated RAW264.7 cell media are aspirated and replaced with fresh serum-free DMEM or PBS. Cells are treated with DMSO vehicle, indomethacin (3 µM), or indomethacin phenethylamide (3 µM) for 30 min at 37° C. followed by the addition of 2-AG (20 µM). After 30 min, medium or PBS is removed and extracted two times with an equal volume of CHCl$_3$:MeOH (2:1). The solvent is evaporated and the residue is dissolved in 1 mL H$_2$O:MeCN (95:5) and applied to a water-charged C18 solid phase extraction column (Varian). Following a water wash, glyceryl prostaglandins are eluted with H$_2$O:MeCN (3:7). The eluant is lyophilized, dissolved in H$_2$O:MeCN (1:1), and subjected to LC/MS analysis. The endogenous 2-AG production and metabolism by RAW264.7 cells can also be measured. To do this, low passage number murine RAW264.7 cells are stimulated with IFN-γ and lipopolysaccharide (LPS) as described above. Activated RAW264.7 cell medium is aspirated and replaced with fresh serum-free DMEM. Cells in a single well of a six-well plate are treated with DMSO vehicle, indomethacin (3 µM), U-73122 (5 µM), or RHC-80267 (100 µM) for 20 min at 37° C. followed by the addition of DMSO vehicle or ionomycin (5 µM). After 20 min, medium is removed and the cells are treated with 8.0 ng pentadeuterated glyceryl prostaglandin standard. Medium is collected and extracted two times with an equal volume of CHCl$_3$:MeOH (2:1). The solvent is evaporated and the residue is redissolved in H$_2$O:MeCN (1:1), filtered (0.22 µm nylon), and subjected to LC/MS analysis.

5.9 Example 9

COX-2 expression and activity are generally linked with the inflammatory process, which accompanies a plethora of pathologies including, but not limited to, arthritis/arthropathy, infectious disease, neurodegenerative disease, neoplasia and autoimmune disease. The quantification of prostaglandin glyceryl esters (PG-Gs) or their metabolites from biological fluids obtained noninvasively (e.g. blood, urine) will allow for the assessment of COX-2 activity in vivo, reflecting both inflammation and disease severity. In addition, serial testing will allow for the tracking of the natural course of the disease as well as the efficacy of anti-inflammatory therapy. A model for this application would be the ubiquitous use of C-reactive protein (CRP) in the diagnosis and assessment of diseases associated with inflammation. The benefits of using PG-Gs in this context instead of more traditional diagnostic markers, such as CRP, involve the highly specific nature of PG-G production. PG-Gs is elevated only when COX-2 activity is elevated whereas CRP elevations, for example, are very non-specific.

Scenario: Elderly woman seeks medical attention for recent onset of joint pain in hands. Urine is collected and PG-G quantification is conducted. PG-Gs are elevated supporting a diagnosis of rheumatoid arthritis. COX-2 inhibitor therapy is initiated (e.g. celecoxib). After one week, symptoms are only mildly relieved and another urine sample reveals PG-G levels are still elevated, indicating that the inflammatory process is still active. Following dosage increase, symptoms are relieved and urinary PG-Gs are normalized.

5.10 Example 10

COX-2 expression and activity are linked to several solid tumors, most notably colorectal adenocarcinoma. The quantification of prostaglandin glyceryl esters (PG-Gs) or their derivatives from biological fluids, described herein, provide a noninvasive "early-warning" for clinically undetectable neoplasia. In addition, serial testing following diagnosis will allow for the tracking of the natural course of the cancer as well as the efficacy of antineoplastic therapy. A model for this application would be the use of prostate specific antigen (PSA) in the diagnosis and assessment of prostate adenocarcinomas. The benefits of PG-G quantification in this context include (a) relative noninvasiveness, (b) sensitivity (most cancers are advanced once symptomatic) and (c) cost (simple lab diagnostic technique versus colonoscopy for example).

Scenario: Elderly asymptomatic man receives annual physical examination. Urine and blood is collected and PG-G quantification is conducted. PG-Gs are elevated in both the urine and plasma, prompting a more detailed search for possible neoplasia. Colonoscopy reveals a single polyp in the descending colon which, following biopsy, proves malignant. Standard chemotherapy is initiated. Following treatment, urinary and plasma PG-G levels have normalized. Annual colonoscopies for 3 years reveal no recurrence. After 3½ years, patient visits physician for an unrelated reason and urinary PG-Gs are quantified. PG-G levels are markedly elevated, indicating the recurrence of carcinoma. The physician recommends colonoscopy, which reveals the presence of carcinoma. Aggressive chemotherapy is initiated and urinary PG-G levels are monitored.

5.11 Example 11

The measurement of PG-Gs from in vitro samples (e.g. cell culture, biopsy samples) allows for the direct quantification of COX-2 activity. Current methods which quantify cyclooxygenase activity do not directly distinguish between COX-1 and COX-2. Methods which quantify COX-2 expression (e.g. Western blotting) do not assess activity which may or may not correlate with expression levels.

Scenario: Researchers investigating new NSAIDS expose cultured cells expressing COX-2 to various concentrations of test compounds for predetermined periods of time. At the conclusion of the exposures, conditioned medium is collected from each culture. The samples of conditioned medium are assayed for the presence of glyceryl-prostaglandin. The researchers find that most of the test compounds have no significant affect on the production of glyceryl-prostaglandin by the cultured cells. However, one compound ("compound X") dramatically reduces the amount of glyceryl-prostaglandin produced by the cultured cells. Therefore, "compound X" is identified as a COX-2 inhibitor. The researchers focus their efforts on "compound X," which may become a new COX-2 specific treatment of inflammatory diseases or cancer. In further experiments, the researchers determine that compound X does not inhibit COX-1. Compound X is, therefore, identified as a COX-2 specific inhibitor.

5.12 Example 12

Figure 19:
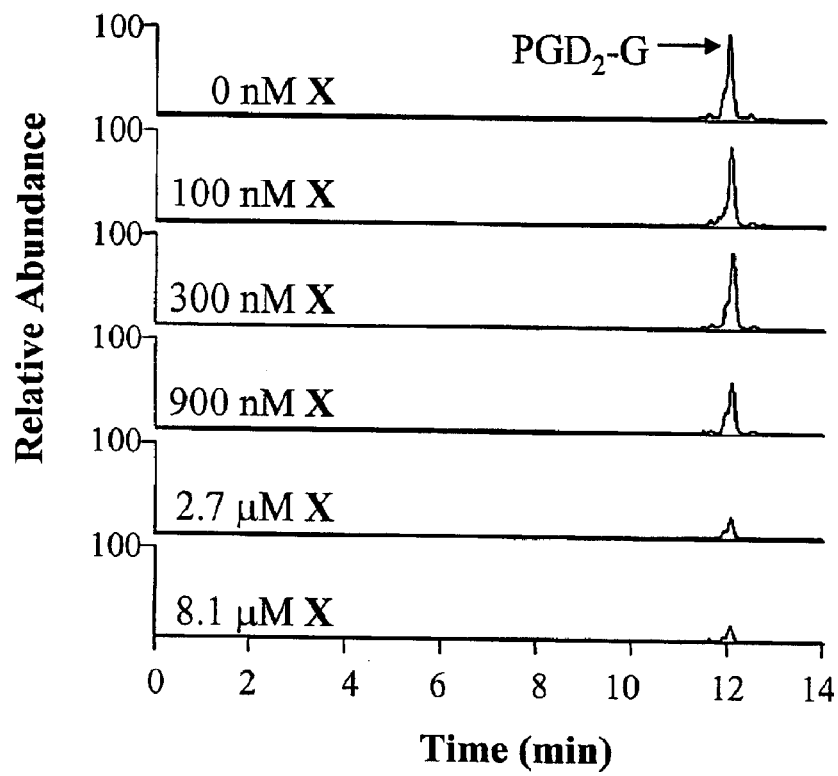
FIG. 19 is an LC/MS graph of PG-Gs produced by RAW264.7 cells treated with an inhibitor of COX-2 activity.
Figure 20:
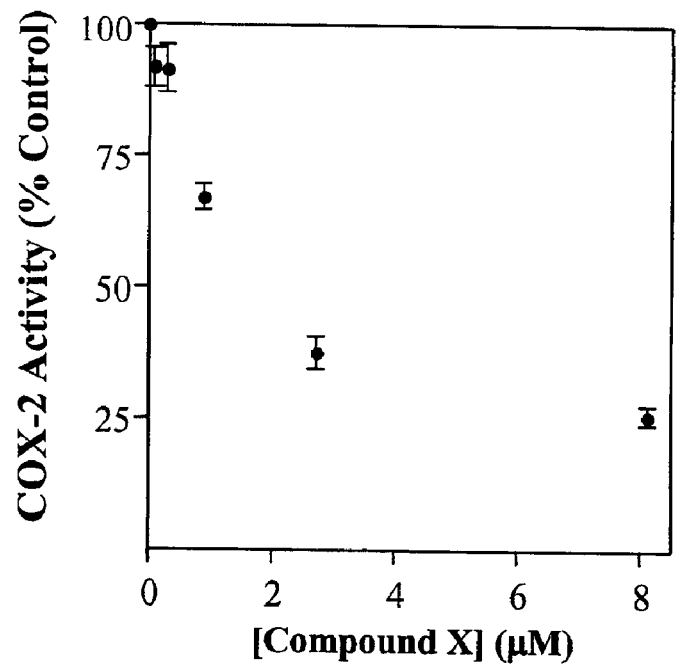
FIG. 20 is a graph showing the inhibitory potency of a test compound on RAW264.7 cells.

In certain embodiments, the present invention can be employed to identify a previously undescribed small molecule modulator of COX-2 activity. This can be done with the following method. Briefly, RAW264.7 cells at 30–40% confluence are activated with lipopolysaccharide (LPS, 20 ng/mL) and treated with a series of concentrations of a test compound. Cells are incubated for 12 h at 37° C. and then medium is removed and replaced with buffered saline. Cells are then treated with 50 µM 2-AG and incubated an additional 30 min at 37° C. Following incubation, buffered saline is collected and treated with pentadeuterated PG-G standard. Buffered saline is extracted twice with equal volumes of 2:1 CHCl$_3$:MeOH. The combined organic extract is evaporated under a stream of argon. The resultant residue is redissolved in 1:1 H$_2$O:MeCN and analyzed by liquid chromatography-mass spectrometry (LC-MS) with selected ion monitoring at m/z=449 (PG-G+Na$^+$) and m/z=454 (PG-G d$_5$+Na$^+$). Quantitation of COX-2 activity is accomplished by comparing the area of the PG-G peak to that of the internal standard. FIG. 19 shows an example of typical selected ion (m/z=449) LC-MS chromatograms of PG-Gs that might be produced by cells treated with the test compound. FIG. 20 shows the inhibitory potency of the test compound (referred to as Compound X,). This compound is selected as a COX-2 inhibitory agent.

REFERENCES

All references, U.S. patents, non U.S. patents, journal articles, and newspaper articles referred to herein are hereby made part of the specification of the present patent and incorporated herein in their entirety by reference. This includes, but is not limited to the following references:

Assay Designs, Inc., 800 Technology Drive, Ann Arbor, Mich. 48108; 734–668–6113; PG, HETE and Tx Immunoassays. Catalog #s 90004, 90104, 91004, 90010, 90110, 90012, 90112, 90072, 90172, 90050, 90051, 90151, 90023 and 90123.

Bisogno, T., Melck, D., De Petrocellis, L., & Di Marzo, V. (1999) J. Neurochem. 72:2113–2119.

DuBois, R N, Radhika, A, Reddy, B S, Entingh, A J. (1996) Gastroenterology 110:1259.

Cohen, et al. U.S. Pat. No. 5,589,575, Purification of hapten-carrier generated antibodies.

Cayman Chemical, 1180 E. Ellsworth Road, Ann Arbor, Mich. 48108; 800-364-9897; Prostaglandin E$_2$ affinity purification kit, Catalog No. 514018.

Eberhart, C E, Coffey, R J, Radhika, A, et al. (1994) Gastroenterology 107:1183.

Fosslien, E. (2000) Ann. Clin. Lab. Sci. 30:3–21.

Jeon, Y J, Yang, K H, Pulaski, J T, & Kaminski, N E. (1996) Mol. Pharmacol. 50:334–341.

Kalgutkar, A S, Kozak, K R, Crews, B C, Hochgesang, Jr. G P, & Marnett, L J. (1998) J. Med. Chem. 41: 4800–4818.

Kalgutkar, A S, Crews, B C, Rowlinson, S W, Marnett, A B, Kozak, K R, Remmel, R P, & Marnett, L J. (2000) Proc. Natl. Acad. Sci. USA 97: 925–930.

Kennedy, B P, Chan, C-C, Culp, S A, & Cromlish, W A. (1993) Biochem. Biophys. Res. Commun. 197:494–500.

Kozak, K R, Rowlinson, S W, & Marnett, L J. (2000) J. Biol. Chem. 275:33744–33749.

Landino, L M, Crews, B C, Timmons, M D, Morrow, J D, & Marnett, L J. (1996) Proc. Natl. Acad. Sci. USA 93:15069–15074.

MacPherson, J C, Pavlovich, J G, & Jacobs, R S. (1996) Biochim. Biophys. Acta 1303:127–136.

Marnett, L J, Siedlik, P H, Ochs, R C, Pagels, W D, Das, M, Honn, K V, Warnock, R H, Tainer, B E, & Eling, T E. (1984) Mol. Pharmacol. 26:328–335.

Masferrer, J L, Zweifel, B S, Manning, P T, Hauser, S D, Leahy, K M, Smith, W G, Isakson, P C, & Seibert, K. (1994) Proc. Natl. Acad. Sci. USA 91, :28–3232.

McCafferty, J, Hoogenboom, H, & Chiswell, D. (1996) Antibody Engineering, a Practical Approach, IRL Press @ Oxford University Press.

Mernaugh, R. & Mernaugh, G. (1994) Methods for the Production of Monoclonal Antibodies, in Molecular Methods in Plant Pathology, Ed by R. P. Singh and U. S. Singh, pg. 343–365.

Mifflin et. al. (2001) The Regulatory Peptide Letter, MedPub, Inc. publishers, Ann Arbor, Mich.; 3(4):49–63.

Odenwaller, R, Chen, Y-N P, & Marnett, L J. (1990) Methods. Enzymol. 187: 479–485.

Prescott (1999) J. Biol. Chem. 274:22901.

Rowlinson, S W, Crews, B C, Lanzo, C A, & Marnett, L J. (1999) J. Biol. Chem. 274: 23305–23310.

Rowlinson, S W, Crews, B C, Goodwin, D C, Schneider, C, Gierse, J K, & Marnett, L J. (2000) J. Biol. Chem. 274:6586–6591

Sheehan, K M, Sheahan, K, O'Donoghue, D P, et al. (1999) JAMA 282:1254.

Sheng, H, Shao, J, Kirkland, S C, et al. (1997) *J. Clin. Invest.* 99:2254.

Smith et al. (2001) *J. Biol. Chem.* 107:1491–1495.

So, O-Y, Scarafia, L E, Mak, A Y, Callan, O H, & Swinney, D C. (1998) *J. Biol. Chem.* 273:5801–5807.

Stella, N., Schweitzer, P., & Piomelli, D. (1997) *Nature* 388:773–778.

Tsujii, M, Kawano, S, Du Bois, R N. (1997) *Proc. Natl. Acad. Sci. USA* 94:3336.

Vane, J R, Mitchell, J A, Appleton, I, Tomlinson, A, Bishop-Bailey, D, Croxtall, J, & Willoughby, D A. (1994) *Proc. Natl. Acad. Sci. USA* 91:2046–2050.

Wadleigh, D J, Reddy, S T, Kopp, E, Ghosh, S, & Herschman, H R. (2000) *J. Biol. Chem.* 275:6259–6266.

Yu, M, Ives, D, & Ramesha C S (1997) *J. Biol. Chem.* 272:21181–21186.

This invention thus being described, it will be obvious that the same may be varied in many ways. Such variations are not to be regarded as a departure from the spirit and scope of the present invention, and all such modifications as would be obvious to one of ordinary skill in the art are intended to be included within the scope of the claims following the detailed description of the invention. The present invention is not bound by theory or mechanism. Thus, although there are described particular embodiments of the present invention of a new and useful "Method for in vitro and in vivo determination of COX-2 activity", it is not intended that such references be construed as limitations upon the scope of this invention except as set forth in the following claims.

What is claimed is:

1. A method of detecting an activity of a COX-2 enzyme in a subject, comprising:
    a) obtaining a sample of the subject; and
    b) detecting a COX-2 specific metabolite of a 2-arachidonylglycerol compound in the sample, wherein the presence of the COX-2 specific metabolite in the sample indicates the activity of the COX-2 enzyme in the subject.

2. The method of claim 1, wherein the metabolite comprises a prostaglandin-glycerol ester.

3. The method of claim 1, wherein the metabolite is selected from a group consisting of: prostaglandin $H_2$-glycerol ester, prostaglandin $E_2$-glycerol ester, 15-keto-prostaglandin $E_2$-glycerol ester, 13,14-dihydro-15-keto-prostaglandin $E_2$-glycerol ester, prostaglandin $D_2$-glycerol ester, prostaglandin $F_{2\alpha}$-glycerol ester, thromboxane $A_2$-glycerol ester, thromboxane $B_2$-glycerol ester, prostacyclin-glycerol ester, 6-keto-prostalandin $F_{1\alpha}$-glycerol ester, prostanglandin $A_2$-glycerol ester, and prostaglandin $B_2$-glycerol ester.

4. The method of claim 1, wherein the metabolite comprises a 6-keto-prostaglandin $F_{1\alpha}$-glycerol ester.

5. The method of claim 1, wherein the subject comprises a human.

6. The method of claim 1, wherein the subject comprises a non-human mammal.

7. The method of claim 1, wherein the subject comprises a cultured cell.

8. The method of claim 1, wherein the detecting step includes generating a mass spectrum of the metabolite.

9. The method of claim 1, wherein the sample comprises urine.

10. The method of claim 1, wherein the sample comprises plasma.

11. The method of claim 1, wherein the sample is selected from a group consisting of: cerebrospinal fluid, saliva, sputum, bile, joint fluid, biopsy, and conditioned media from a cell culture.

12. A method of measuring an activity of a COX-2 enzyme in a subject, comprising:
    a) obtaining a sample of the subject;
    b) measuring an amount of a COX-2 specific metabolite of a 2-arachidonylglycerol compound in the sample; and
    c) relating the amount of the COX-2 specific metabolite to the activity of the COX-2 enzyme.

13. The method of claim 12, further comprising comparing the amount measured to a standard value, which correlates to an amount of signal with a known amount of a COX-2 specific metabolite of a 2-arachidonyiglycerol compound.

14. The method of claim 12, further comprising generating a standard curve.

15. The method of claim 12, wherein the metabolite comprises a prostaglandin-glycerol ester.

16. The method of claim 12, wherein the metabolite comprises a 6-keto-prostaglandin $F_{1\alpha}$-glycerol ester.

17. The method of claim 12, wherein the subject comprises a human.

18. The method of claim 12, wherein the measuring step includes generating a mass spectrum of the metabolite.

19. The method of claim 12, wherein the sample comprises urine.

20. The method of claim 12, wherein the sample comprises plasma.

21. The method of claim wherein the sample is selected from a group consisting of: cerebrospinal fluid, saliva, sputum, bile, joint fluid, biopsy, and conditioned media from a cell culture.

22. A method of analyzing COX-2 enzyme activity in a human subject, comprising:
    a) obtaining a sample of a subject; and
    b) detecting a prostaglandin-glycerol ester comprising metabolite of a COX-2 selective substrate in the sample, wherein the presence of the metabolite in the sample indicates the activity of the COX-2 enzyme in the subject.

23. The method of claim 22, further comprising:
    c) measuring an amount of the metabolite in the sample.

24. The method of claim 23, further comprising relating the amount of the metabolite in the sample to the activity of the COX-2 enzyme in the subject, and relating said amount of the COX-2 specific metabolite to the activity of the COX-2 enzyme.

25. The method of claim 22, wherein the metabolite comprises a 6-keto-prostaglandin $F_{1\alpha}$-glycerol ester.

26. The method of claim 22, wherein the detecting step includes generating a mass spectrum of the metabolite.

27. The method of claim 22, wherein the sample comprises urine.

28. The method of claim 22, wherein the sample comprises plasma.

29. The method of claim 22, wherein the sample is selected from a group consisting of: cerebrospinal fluid, saliva, sputum, bile, joint fluid, biopsy, and conditioned media from a cell culture.

30. A method of determining COX-2 activity in a sample, comprising:
    a) adding an arachidonyiglycerol ester comprising COX-2 selective substrate to the sample; and
    b) detecting a metabolite of the COX-2 selective substrate in the sample, wherein the presence of the metabolite indicates activity of the COX-2 enzyme in the sample.

31. The method of claim 30 further comprising relating the amount of the metabolite to the activity of the COX-2 enzyme.

32. The method of claim 30, wherein the metabolite comprises a prostaglandin-glycerol ester.

33. The method of claim 30, wherein the metabolite is selected from a group consisting of: prostaglandin $H_2$-glycerol ester, prostaglandin $E_2$-glycerol ester, 15-keto-prostaglandin $E_2$-glycerol ester, 13,14-dihydro-15-keto-prostaglandin $E_2$-glycerol ester, prostaglandin $D_2$-glycerol ester, prostaglandin $F_{2\alpha}$-glycerol ester, thromboxane $A_2$-glycerol ester, thromboxane $B_2$-glycerol ester, prostacyclin-glycerol ester, 6-keto-prostaglandin $F_{1\alpha}$-glycerol ester, prostaglandin $A_2$-glycerol ester, and prostaglandin $B_2$-glycerol ester.

34. The method of claim 1, wherein the metabolite comprises a 6-keto-prostaglandin $F_{1\alpha}$-glycerol ester.

35. The method of claim 22, wherein the patient is in need of diagnosis of, or monitoring of an inflammatory disease state.

36. The method of claim 22, wherein the patient is in need of diagnosis of, or monitoring of the presence of cancer.

37. The method of claim 22, wherein the patient is need of monitoring anticancer therapy effectiveness.

* * * * *

UNITED STATES PATENT AND TRADEMARK OFFICE
CERTIFICATE OF CORRECTION

PATENT NO.       : 7,189,504 B2                                        Page 1 of 1
APPLICATION NO.  : 09/923637
DATED            : March 13, 2007
INVENTOR(S)      : Marnett et al.

It is certified that error appears in the above-identified patent and that said Letters Patent is hereby corrected as shown below:

Column 1, line 28:

"National Foundation for Cancer Research." should be --National Foundation for Cancer Research Grant numbers CA047479 and CA 089450.--

Signed and Sealed this

Fifth Day of June, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,189,504 B2 | Page 1 of 1 |
| APPLICATION NO. | : 09/923637 | |
| DATED | : March 13, 2007 | |
| INVENTOR(S) | : Marnett et al. | |

It is certified that error appears in the above-identified patent and that said Letters Patent is hereby corrected as shown below:

Column 26, line 27,

"Claim 21. The method of claim wherein the sample is selected from a group consisting of: cerebrospinal fluid, saliva, sputum, bile, joint fluid, biopsy, and conditioned media from a cell culture."

should be

-- Claim 21. The method of claim 12, wherein the sample is selected from a group consisting of: cerebrospinal fluid, saliva, sputum, bile, joint fluid, biopsy, and conditioned media from a cell culture. --

Signed and Sealed this

Sixteenth Day of February, 2010

David J. Kappos
*Director of the United States Patent and Trademark Office*